US008951528B2

(12) United States Patent
Stoermer et al.

(10) Patent No.: US 8,951,528 B2
(45) Date of Patent: Feb. 10, 2015

(54) IMMUNE RESPONSE MODIFIER CONJUGATES

(75) Inventors: Doris Stoermer, Newbury Park, CA (US); George W. Griesgraber, Eagan, MN (US); James D. Mendoza, N. Robbinsdale, MN (US); Jason D. Bonk, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 1403 days.

(21) Appl. No.: 12/280,472

(22) PCT Filed: Feb. 21, 2007

(86) PCT No.: PCT/US2007/004673
§ 371 (c)(1),
(2), (4) Date: Aug. 22, 2008

(87) PCT Pub. No.: WO2007/100634
PCT Pub. Date: Sep. 7, 2007

(65) Prior Publication Data
US 2009/0035323 A1 Feb. 5, 2009

Related U.S. Application Data

(60) Provisional application No. 60/775,468, filed on Feb. 22, 2006.

(51) Int. Cl.
*A61K 39/44* (2006.01)
*A61K 39/385* (2006.01)
*A61K 47/48* (2006.01)
*A61K 31/4745* (2006.01)

(52) U.S. Cl.
CPC ....... *A61K 47/48538* (2013.01); *A61K 31/4745* (2013.01); *A61K 47/48384* (2013.01)
USPC .................. 424/178.1; 424/193.1; 424/194.1

(58) Field of Classification Search
None
See application file for complete search history.

(56) References Cited

U.S. PATENT DOCUMENTS

| | | | |
|---|---|---|---|
| 4,689,338 A | 8/1987 | Gerster | |
| 4,929,624 A | 5/1990 | Gerster et al. | |
| 5,238,944 A | 8/1993 | Wick et al. | |
| 5,266,575 A | 11/1993 | Gerster et al. | |
| 5,268,376 A | 12/1993 | Gerster | |
| 5,346,905 A | 9/1994 | Gerster | |
| 5,352,784 A | 10/1994 | Nikolaides et al. | |
| 5,389,640 A | 2/1995 | Gerster et al. | |
| 5,446,153 A | 8/1995 | Lindstrom et al. | |
| 5,482,936 A | 1/1996 | Lindstrom | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,110,929 A | 8/2000 | Gerster et al. | |
| 6,113,918 A | 9/2000 | Johnson et al. | |
| 6,194,388 B1 | 2/2001 | Krieg et al. | |
| 6,194,425 B1 | 2/2001 | Gerster et al. | |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,303,347 B1 | 10/2001 | Johnson et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,451,810 B1 | 9/2002 | Coleman et al. | |
| 6,476,000 B1 | 11/2002 | Agrawal | |
| 6,518,265 B1 | 2/2003 | Kato et al. | |
| 6,525,028 B1 | 2/2003 | Johnson et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,573,273 B1 | 6/2003 | Crooks et al. | |
| 6,649,172 B2 | 11/2003 | Johnson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |

(Continued)

FOREIGN PATENT DOCUMENTS

EP 0 394 026 10/1990
WO WO 00/75304 12/2000

(Continued)

OTHER PUBLICATIONS

Heit et al (J. Immunology 170:2802-2805, 2003).*
Heil et al., *Science*, vol. 303, pp. 1526-1529, Species-Specific Recognition of Single-Stranded RNA via Toll-Like Receptor 7 and 8:, Mar. 5, 2004.
Hermanson, G. (1996), *Bioconjugate Techniques*, Academic Press, Chapter 5 "Heterobifunctional Cross-Linkers", p. 228-285.
Hermanson, G. (1996), *Bioconjugate Techniques*, Academic Press, p. 114-116.
Hermanson, G. (1996), *Bioconjugate Techniques*, Academic Press, p. 76-79.
King et. al, *J. Med. Chem.*, 2002, 45, entitled Monoclonal Antibody Conjugates of Doxorubicin Prepared With Branched Peptide Linkers: Inhibition of Aggregation by Methoxytriethyleneglycol Chains, pp. 4336-4343.
Toki, B. E. et al. *J. Org. Chem.*, 2002, 67, 1866-1872, "Protease-Mediated Fragmentation of p-Amidobenzyl Ethers: A New Strategy for the Activation of Anticancer Prodrugs".

(Continued)

*Primary Examiner* — Robert A Zeman

(57) ABSTRACT

The present invention provides IRM conjugates that includes an IRM moiety and a second active moiety covalently linked to the IRM moiety in which the covalent link does not depend on UV irradiation.

7 Claims, 5 Drawing Sheets

(56) References Cited

U.S. PATENT DOCUMENTS

| | | | |
|---|---|---|---|
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,756,382 B2 | 6/2004 | Coleman et al. | |
| 6,797,718 B2 | 9/2004 | Dellaria et al. | |
| 6,818,650 B2 | 11/2004 | Griesgraber | |
| 7,163,947 B2 | 1/2007 | Griesgraber et al. | |
| 7,387,271 B2 | 6/2008 | Noelle et al. | |
| 7,427,629 B2 * | 9/2008 | Kedl et al. | 514/279 |
| 2003/0139364 A1 | 7/2003 | Krieg et al. | |
| 2003/0185835 A1 | 10/2003 | Braun | |
| 2003/0199461 A1 | 10/2003 | Averett et al. | |
| 2003/0199538 A1 | 10/2003 | Skwierczynski et al. | |
| 2004/0091491 A1 | 5/2004 | Kedl et al. | |
| 2004/0141950 A1 | 7/2004 | Noelle et al. | |
| 2004/0147543 A1 | 7/2004 | Hays et al. | |
| 2004/0176367 A1 | 9/2004 | Griesgraber et al. | |
| 2004/0258698 A1 | 12/2004 | Wightman et al. | |
| 2005/0107322 A1 | 5/2005 | O'Hagan et al. | |
| 2005/0136065 A1 | 6/2005 | Valiante, Jr. | |
| 2005/0287155 A1 | 12/2005 | Santi et al. | |
| 2006/0045885 A1 | 3/2006 | Kedl et al. | |
| 2006/0100229 A1 | 5/2006 | Hays et al. | |
| 2006/0210588 A1 | 9/2006 | Bachmann et al. | |
| 2008/0193468 A1 | 8/2008 | Levy et al. | |
| 2009/0028874 A1 | 1/2009 | Van Der Burg et al. | |

FOREIGN PATENT DOCUMENTS

| | | |
|---|---|---|
| WO | WO 02/08905 | 1/2002 |
| WO | WO 02/24225 | 3/2002 |
| WO | WO 03/094836 | 11/2003 |
| WO | WO 2004032829 A2 * | 4/2004 |
| WO | WO 2005/018551 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/065673 | 7/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/082023 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028545 | 3/2006 |
| WO | WO 2006/028962 | 3/2006 |
| WO | WO 2006/029115 | 3/2006 |
| WO | WO 2006/038923 | 4/2006 |
| WO | WO 2006/065280 | 6/2006 |
| WO | WO 2006/074003 | 7/2006 |
| WO | WO 2006/083440 | 8/2006 |
| WO | WO 2006/086449 | 8/2006 |
| WO | WO 2006/086633 | 8/2006 |
| WO | WO 2006/086634 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO 2006/091720 | 8/2006 |
| WO | WO 2006/093514 | 9/2006 |
| WO | WO 2006/098852 | 9/2006 |
| WO | WO 2006/107771 | 10/2006 |
| WO | WO 2006/107851 | 10/2006 |
| WO | WO 2006/107853 | 10/2006 |

OTHER PUBLICATIONS

Jeffrey, S. C. et al.; *J. Med. Chem.*, 2005, 48, "Design, Synthesis, and in Vitro Evaluation of Dipeptide-Based Antibody Minor Groove Binder Conjugates", 1344-1358.

Sun, M. M. C. et al., *Bioconjugate Chem.* 2005, 16, Entitled Reduction-Alkylation Strategies for the Modification of Specific Monoclonal antibody Disulfides, 1282-1290.

T. W. Greene and P. G. M. Wuts, *Protective Groups in Organic Synthesis*, John Wiley & Sons, New York, USA, 1991.

T. Higuchi and W. Stella, "Pro-drugs as Novel Delivery Systems," vol. 14 of the A. C. S. Symposium Series, and in Bioreversible Carriers in Drug Design, ed. Edward B. Roche, American Pharmaceutical Association and Pergamon Press, 1987.

C. Bertozzi and M. Bednarski, *J. Org. Chem.* 1991, 56, "The Synthesis of Heterobifunctional Linkers for the Conjugation of Ligands to Molecular Probes," 4326-4329.

A. Bray et al. Aust. J. Chem. 1990, 43, DNA-Binding Compounds, III Synthesis of a Peptide-Linked Binuclear Platinum-Terpyridine Complex, 629-634.

Hamajima et al. A Macromolecular Multicomponent Peptide Vaccine Prepared Using the Gluteraldehyde Conjugation Method with Strong immunogicity for HIV-1, Clinical Immunology and Immunopathology, Dec. 1995, vol. 77, No. 3, p. 374-379.

TE Piao King et al: Preparation of Protein Conjugates via Intermolecular Disulfide Bondformation, Biochemistry, American Chemical Society, US, vol. 17, No. 8, Jan. 1, 2008, pp. 1499-1506.

Huang et al: "A Polyethylene Glycol Copolymer for Carrying and Releasing Multiple Copies of Cysteine-Containing Peptides," Bioconjugate Chemistry, ACS, Washington, DC, US, vol. 9, No. 5, Sep. 1, 1998, pp. 612-617.

Supplementary European Search report from Application No. EP07757438, Jun. 17, 2011.

* cited by examiner

IMMUNE RESPONSE MODIFIER CONJUGATES

CROSS REFERENCE TO RELATED APPLICATIONS

This application is a national stage filing under 35 U.S.C. 371 of PCT/US2007/004673, filed Feb. 21, 2007, which claims priority to U.S. Provisional Application No. 60/775,468, filed Feb. 22, 2006, the disclosure of which is incorporated by reference in its/their entirety herein.

BACKGROUND

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929; and International Publication Number WO2005/079195) and more are still being discovered. Other IRMs have higher molecular weights, such as oligonucleotides, including CpGs (see, e.g., U.S. Pat. No. 6,194,388).

Many IRMs may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H2$-mediated diseases (e.g., asthma, allergic rhinitis, atopic dermatitis), auto-immune diseases, and are also useful as vaccine adjuvants.

In some cases, an IRM compound may be administered in a conjugated composition in which the IRM compound is covalently attached to an antigenic moiety through a UV-activatable linker (see, e.g., United States Patent Publication No. 2004/0091491). Covalently attaching an IRM compound to an antigenic moiety can increase the likelihood that the IRM compound and an associated antigen are co-delivered to a target cell such as, for example, an immune cell. Co-delivering an IRM compound and an antigen to an immune cell can increase the immune response to the antigen and improve antigen-specific immunological memory.

In view of the great therapeutic potential for IRMs, and despite the important work that has already been done, there is a substantial ongoing need to expand their uses and therapeutic benefits, and to develop additional compositions for delivery.

SUMMARY

Additional methods have been developed for making immunomodulatory conjugates that include an IRM moiety covalently linked to a second moiety having a desired biological activity, i.e., IRM conjugates.

Accordingly, the present invention provides an IRM conjugate that includes an IRM moiety and a second active moiety covalently linked to the IRM moiety in which the covalent link does not depend on UV irradiation.

In some embodiments, the covalent link includes a disulfide linkage, a thioether linkage, a hydrazone linkage, an oxime linkage, an amide linkage, a urea linkage, a thiourea linkage, a carbamate linkage, a hydrazine linkage, a hydroxyl amine linkage, or a nitrone linkage.

In another aspect, the present invention also provides a method of stimulating an antigen-specific immune response in a subject. Generally, the method includes administering to the subject an IRM conjugate that includes an IRM moiety covalently linked to an antigenic moiety, wherein formation of the covalent link does not depend on UV irradiation.

In another aspect, the present invention also provides a method of targeted delivery of an IRM conjugate. Generally, the method includes administering to the subject an IRM conjugate that includes an IRM moiety covalently linked to a targeting moiety, wherein formation of the covalent link does not depend on UV irradiation.

In another aspect, the present invention also provides a method of making an IRM conjugate. Generally, the method includes covalently attaching a first linker having a first functional group to an IRM compound having immunomodulatory activity, at a site on the IRM compound selected to preserve at least a portion of the immunomodulatory activity of the IRM compound, thereby forming an IRM moiety; and allowing the IRM moiety to react with a second moiety having biological activity and a second functional group by forming a covalent bond between the first functional group and the second functional group, thereby forming an IRM conjugate that possesses IRM activity and the biological activity of the second moiety.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
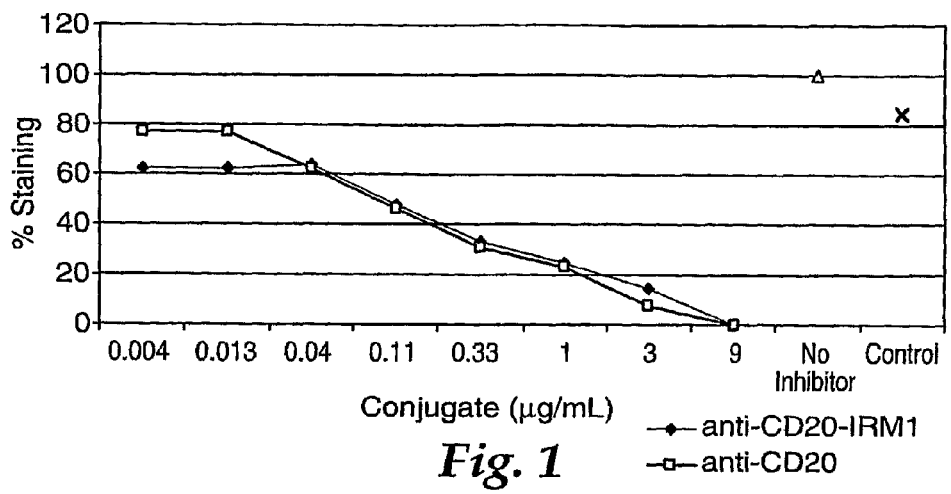
FIG. 1 is a line graph showing anti-CD20 activity of an IRM/anti-CD20 antibody conjugate.
Figure 2:
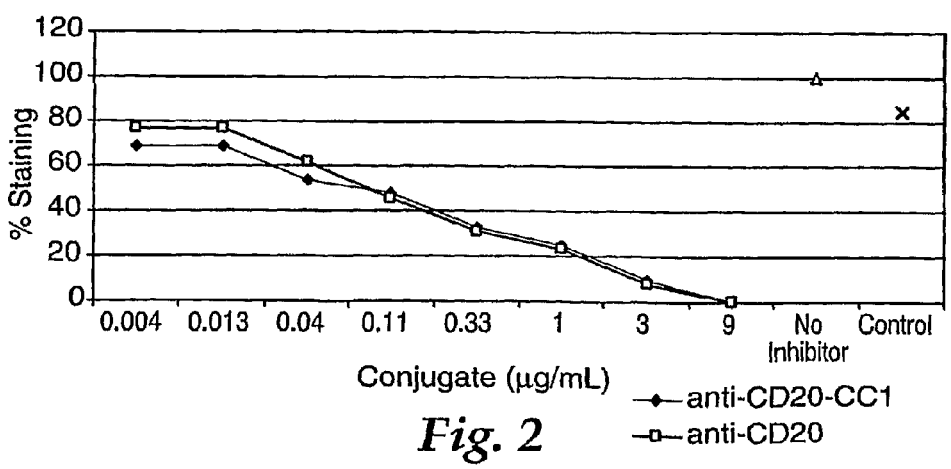
FIG. 2 is a line graph showing anti-CD20 activity of anti-CD20 antibody conjugated to a control compound.
Figure 3:
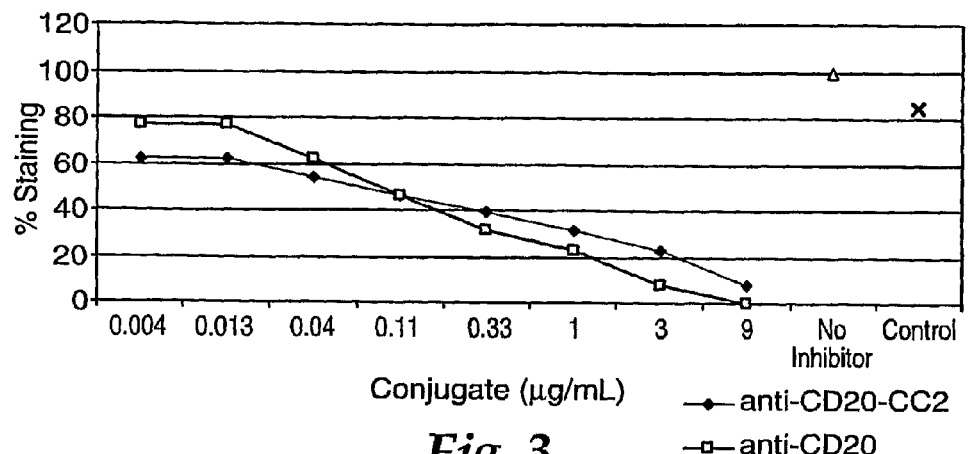
FIG. 3 is a line graph showing anti-CD20 activity of anti-CD20 antibody conjugated to a control compound.
Figure 4:
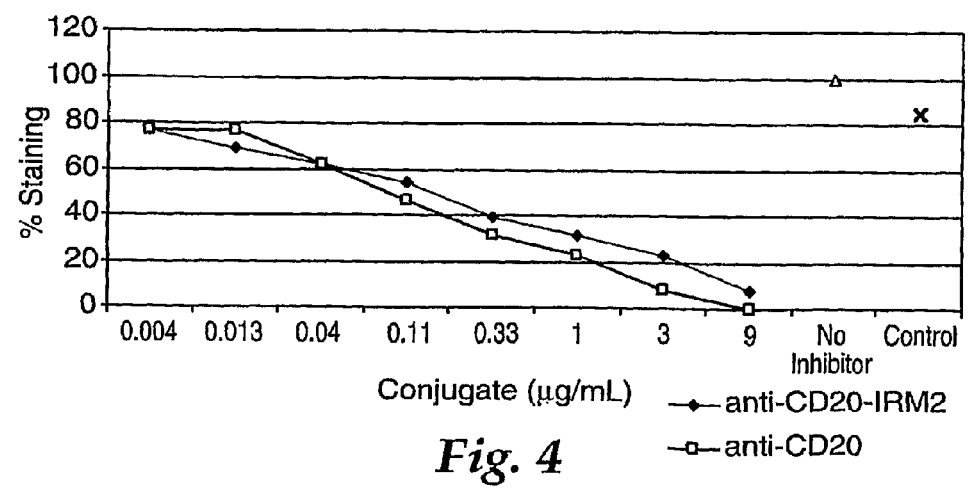
FIG. 4 is a line graph showing anti-CD20 activity of an IRM/anti-CD20 antibody conjugate.

The present invention relates to novel immune response modifier (IRM) conjugates and the methods used to make IRM conjugates. The invention also relates to methods of generating an immune response using the IRM conjugates. Generating an immune response using an IRM conjugate can lead to improved treatments for certain types of diseases such as, for example, certain infectious diseases and cancers.

Co-delivering an IRM compound and an antigen to a single immune cell can increase the immune response directed against the antigen. It can also improve immunological memory so that the immune system is better able to protect against disease if one is re-exposed to the antigen, which may occur if, for example, one is reinfected by a pathogen or a tumor relapses.

Known methods of making conjugates that link an IRM to an antigen use UV irradiation to react an IRM moiety with the antigen. It is difficult, if not impossible, to control the number and location of IRM moieties that attach to the antigen in this method.

The present invention uses chemistry that does not depend upon UV irradiation to link an IRM moiety and a second moiety that has biological activity (e.g., an antigen). Instead, the present invention uses chemistry that makes it easier to control the conjugation reaction, control the ratio of IRM moiety to second active moiety, characterize the final conjugate, and obtain a more uniform product.

As used herein, the following terms shall have the indicated meanings:

"Agonist" refers to a compound that can combine with a receptor (e.g., a TLR) to induce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist) or a particular combination of TLRs (e.g., a TLR 7/8 agonist—an agonist of both TLR7 and TLR8).

"Ameliorate" refers to any reduction in the extent, severity, frequency, and/or likelihood of a symptom or clinical sign characteristic of a particular condition.

"Antigen" refers to any substance that may be bound by an antibody in a manner that is immunospecific to some degree.

"Antigenic activity" includes one or more of the following: generation of antibodies specific to the antigen by B cells, immune cell maturation, cytokine production by immune cells, and generation of antigen-presenting cells that present the antigen.

"Antigenic moiety" refers to that portion of an immunomodulatory conjugate that possesses antigenic activity. An antigenic moiety may be, or be derived from, an antigen. In some cases, the term "antigenic moiety" may refer to an uncoupled antigenic compound prior to coupling to, or after decoupling from, an IRM moiety.

"Immune cell" refers to cell of the immune system, i.e., a cell directly or indirectly involved in the generation or maintenance of an immune response, whether the immune response is innate, acquired, humoral, or cell-mediated.

"Immunomodulatory" and variations thereof refer to any increase or decrease (i.e., induction or inhibition) of immune activity.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Inhibit" and variations thereof refer to any measurable reduction of cellular activity. For example, inhibition of a particular cytokine refers to a decrease in production of the cytokine. The extent of inhibition may be characterized as a percentage of a normal level of activity.

"IRM compound" refers generally to an immune response modifier compound that alters the level of one or more immune regulatory molecules, e.g., cytokines or co-stimulatory markers, when administered to an IRM-responsive cell. Representative IRM compounds include, for example, the small organic molecules, purine derivatives, small heterocyclic compounds, amide derivatives, oligonucleotide sequences, and aminoalkyl glucosaminide phosphates described below.

"IRM moiety" refers to that portion of an immunomodulatory conjugate that possesses immunomodulatory activity. The IRM moiety may be, or be derived from, an IRM compound, but may, alternatively, be or be derived from some other immunomodulatory material. In some cases, the term "IRM moiety" may refer to an uncoupled compound prior to coupling to, or after uncoupling from, a target-specific moiety.

"Marker" and variations thereof refer to any substance on a cell surface that may be bound by a ligand in a manner that is specific to some degree. As used herein, a marker-ligand interaction explicitly excludes immunological affinity—i.e., antibody-antigen affinity binding. Thus, some substances on the cell surface may be considered a marker (i.e., it may be capable of non-immunological receptor-ligand binding) in one context and an antigen in another context (i.e., it may be the target of an antibody).

"Polypeptide" refers to a sequence of amino acid residues without regard to the length of the sequence. Therefore, the term "polypeptide" refers to any amino acid sequence having at least two amino acids and includes full-length proteins and, as the case may be, polyproteins.

"Prophylactic" and variations thereof refer to a treatment that limits, to any extent, the development and/or appearance of a symptom or clinical sign of a condition.

"Proteinaceous" and variations thereof refer to materials that have the nature and/or character of proteins or polypeptides.

"Selective" and variations thereof refer to having a differential or a non-general impact on biological activity. An agonist that selectively modulates biological activity through a particular TLR may be a TLR-selective agonist. TLR-selectivity may be described with respect to a particular TLR (e.g., TLR8-selective or TLR7-selective) or with respect to a particular combination of TLRs (e.g., TLR 7/9-selective).

"Sign" or "clinical sign" refers to an objective physical finding relating to a particular condition capable of being found by one other than the patient.

"Specific" and variations thereof refer to having a differential or a non-general (i.e., non-specific) affinity, to any degree, for a particular target.

"Symptom" refers to any subjective evidence of disease or of a patient's condition.

"Target-specific moiety" refers to that portion of an immunomodulatory conjugate that possesses target-specific affinity. The target-specific moiety may be, or be derived from, an antibody, but may, alternatively, be or be derived from a non-antibody protein or peptide, or even non-protein material. In some cases, the term "target-specific moiety" may refer to an uncoupled compound prior to coupling to, or after uncoupling from, an IRM moiety.

"Therapeutic" and variations thereof refer to a treatment that ameliorates one or more existing symptoms or clinical signs associated with a condition.

"Treat" or variations thereof refer to reducing, limiting progression, ameliorating, preventing, or resolving, to any extent, the symptoms or signs related to a condition.

As used herein, "a," "an," "the," "at least one," and "one or more" are used interchangeably. Thus, for example, an IRM conjugate comprising "an" IRM moiety can be interpreted to mean that the IRM conjugate includes one or more IRM moieties.

Also herein, the recitations of numerical ranges by endpoints include all numbers subsumed within that range (e.g., 1 to 5 includes 1, 1.5, 2, 2.75, 3, 3.80, 4, 5, etc.).

The IRM conjugates of the present invention include an IRM moiety and a second active moiety covalently linked to the IRM moiety in which the covalent link does not depend on UV irradiation. Thus, IRM conjugates may be designed to possess at least one IRM activity and at least one additional biological activity characteristic of the second active moiety of the conjugate.

One aspect of IRM activity is modulation of cytokine biosynthesis. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265). IRM activity also can affect other aspects of the innate immune response. For example, IRM activity can include stimulating natural killer cell activity, an effect that may be due to cytokine induction. IRM activity also may include activating macrophages, which in turn stimulate secretion of nitric oxide and the production of additional cytokines. IRM activity also may include inducing cytokine production by T cells, activating T cells specific to an antigen, and/or activating dendritic cells. Further, IRM activity may include proliferation and differentiation of B-lymphocytes.

IRM activity also can affect the acquired immune response. For example, IRM activity can include inducing the production of the T helper type 1 ($T_H1$) cytokine IFN-γ and/or inhibiting the production of the T helper type 2 ($T_H2$) cytokines IL-4, IL-5 and/or IL-13.

The IRM moiety of an IRM conjugate need not possess the full magnitude of IRM activity possessed by the corresponding uncoupled IRM compound. In other words, the IRM moiety may possess measurable IRM activity that can be less than, roughly equivalent to, or greater than the IRM activity possessed by the corresponding free IRM compound.

The IRM activity of the IRM moiety may result in the generation of an immune response. The particular utility of the immune response induced by a particular IRM conjugate may be influenced, at least in part, by the nature of the second moiety of the IRM conjugate. For example, if the second moiety possesses antigenic activity, the IRM conjugate may induce an antigen-specific immune response. Alternatively, if the second moiety possesses targeting activity, the IRM conjugate may be used to deliver IRM activity to a selected target cell population.

Thus, the present invention also provides a method of stimulating an antigen-specific immune response in a subject. Generally, the method includes administering to the subject an IRM conjugate that includes an IRM moiety covalently linked to an antigenic moiety. Administering such an IRM conjugate to a subject can elicit an immune response that is specifically directed against the antigenic material of the antigenic moiety. Thus, an IRM conjugate that includes an antigenic moiety that is, or is derived from, an antigen that is associated with a particular disease may be useful for eliciting an antigen-specific immune response against the antigen. Such an immune response may provide prophylactic and/or therapeutic treatment of the disease associated with the antigenic material of the antigenic moiety. For example, an IRM conjugate in which an IRM moiety is covalently linked to an antigenic moiety containing an HIV antigen may provide therapeutic and/or prophylactic (e.g., provide protection against infection) treatment for HIV. As another example, an IRM conjugate that includes an IRM moiety and an antigenic moiety containing a tumor-associated antigen may provide therapeutic and/or prophylactic treatment against a tumor associated with the antigen.

An antigenic moiety may be, or be derived from, any suitable antigenic material. In various embodiments, suitable antigenic material may elicit a cell-mediated immune response, a humoral immune response, or both. Suitable antigenic material may be synthetic or occur naturally and, when naturally occurring, may be endogenous (e.g., a self-antigen) or exogenous. Suitable antigenic materials include but are not limited to peptides or polypeptides (including a nucleic acid, at least a portion of which encodes the peptide or polypeptide); lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids.

Because many antigenic materials are proteinaceous, it is understood that modifications can be made to a particular antigenic material without rendering the modified antigenic material unsuitable for use as an antigenic moiety. For example, one or more portions of the amino acid sequence of a proteinaceous antigenic material may be deleted or substituted, or additional amino acids may be added to a proteinaceous antigenic material, and the antigenic material can still retain sufficient antigenic character to be suitable for use as an antigenic moiety. Therefore, in the description that follows, reference to a particular proteinaceous antigenic material (e.g., an antigen) includes antigenic materials that have such modifications (e.g., amino acid additions, deletions, and/or substitutions) as are possible while retaining a sufficient amount of antigenic character.

In another aspect, the present invention also provides a method of targeted delivery of an IRM conjugate. Generally, the method includes administering to the subject an IRM conjugate that includes an IRM moiety covalently linked to a targeting moiety. Coupling the IRM moiety to the target-specific moiety can limit systemic availability of the IRM moiety, even when administered via a systemic delivery route. Moreover, the IRM moiety may be concentrated in the vicinity of target immune cells, thereby maturing and activating the immune cells more effectively. Immune cells activated at the site of a tumor—or even inside a tumor mass—may be able to utilize a tumor antigen present on the surface of the tumor cells to initiate an immune response against the tumor. This method could provide a generalized anti-tumor therapy without the need for tumor-specific antibodies. It may also result in more efficacious treatment, thereby permitting use of either less of a particular IRM or a less active IRM. Thus, more IRM compounds may be considered clinically useful when administered as part of a targeted IRM conjugate, thereby providing greater flexibility and more treatment options.

In some cases, the target-specific moiety may be an antibody or be derived from an antibody (i.e., at least enough of the immunospecific portion of an antibody—e.g., enough of a light chain—to provide some degree of immunospecificity). However, in other cases, the target-specific moiety may be, or be derived from, an agent that recognizes at least a portion of a tumor-specific marker such as, for example, a ligand that binds to a receptor that is, to some extent, specifically expressed by the target cell population. In this example, the receptor may be considered a tumor-specific marker.

In some embodiments, an IRM moiety may be coupled to an anti-tumor target-specific moiety such as, for example, an anti-tumor antibody or a ligand of a tumor-specific marker. As used herein, an anti-tumor antibody refers to an antibody (Ab) that recognizes cells of a tumor with some degree of specificity over normal tissue cells. The coupled IRM-Ab conjugate exploits the tumor specificity provided by the antibody to target delivery of the coupled IRM moiety to the vicinity of tumor antigens. Thus, immune cells in the vicinity of the tumor—as opposed to immune cells throughout the patient—are preferentially activated, thereby generating a localized tumor-specific immune response while limiting systemic activation of immune cells. Therapy employing a coupled IRM/tumor-specific conjugate may be particularly desirable for treatment of cancers (e.g., metastatic cancers) that are difficult or impossible to treat by other therapies such as, for example, surgery, radiotherapy, etc.

In other embodiments, the IRM moiety may be coupled to a target-specific moiety that recognizes, for example, an endothelial target. Significant differences exist in the endothelium environments of tumor masses compared to normal capillary beds. Differences exist, for example, in the identity and extent to which certain endothelial surface proteins, adhesion molecules (e.g., integrins), extracellular matrix proteins, growth factor receptors, etc. are expressed. These differences can be exploited to target delivery of an IRM moiety to tumor-related endothelium. Some reagents that specifically target such differences have been demonstrated to be useful as anti-angiogenic therapies. Coupling such an agent, as a target-specific moiety, to an IRM moiety can combine two effective anti-tumor therapies: immunotherapy and anti-angiogenesis therapy.

The use of anti-angiogenic reagents in this way may offer the promise of combined anti-angiogenesis and immunotherapy. Additionally, targeted delivery of an IRM to the tumor endothelium, as opposed to the tumor itself, may provide more effective long-term treatment since, generally, the endothelium is a less mutagenic tissue than a tumor mass. Therefore, therapy directed toward the endothelium may be far less likely to cause drug resistance. Also, a therapy directed toward the endothelium may be effective against virtually any vascularized tumor (e.g., breast cancer, prostate cancer, lung cancer) without the need for tumor-specific reagents.

In still other alternative embodiments, the target-specific moiety may include two or more target-specific moieties, each of which could bind to a different target. Thus, for example, a target-specific moiety may include one target-specific moiety that recognizes, for example, an immune cell antigen or co-stimulatory marker (e.g., a dendritic cell target) and a second target-specific moiety (e.g., an anti-tumor antigen) that recognizes, for example, target tumor cells. Such an IRM conjugate may not only target delivery of the IRM moiety to either or both target cell populations, but also may provide targeted delivery of the target immune cell (e.g., dendritic cell or tumor-killing cell) and IRM moiety to the vicinity of the target tumor cells (e.g., a tumor).

The target-specific moiety of the IRM conjugate may be any material that can provide targeted delivery of the conjugate. In many embodiments, the target-specific portion may provide immunospecific targeting, i.e., may be a sufficient portion of an immunoglobulin (i.e., an antibody) to promote immunospecific binding of the IRM conjugate to a target antigen. However, non-immunoglobulin target-specific materials such as, for example, receptor ligands (natural or synthetic), lipids, etc. may be used as well. Exemplary suitable target-specific moieties, including antibodies and non-immunoglobulin target-specific materials, are described, for example, in International Publication No. WO2006/091720.

Because immunoglobulins are proteins, it is understood that modifications can be made to a particular immunoglobulin without rendering the modified immunoglobulin unsuitable for use as a targeting moiety. For example, one or more portions of the immunoglobulin amino acid sequence may be deleted or substituted, or additional amino acids may be added to an immunoglobulin, and the immunoglobulin can still retain sufficient immunospecific character to be suitable for use as a targeting moiety. Therefore, in the description that follows, reference to a particular antibody includes immunoglobulins that have such modifications (e.g., amino acid additions, deletions, and/or substitutions) as are possible while retaining a sufficient amount of immunospecific character.

Suitable antibodies may be specific for microbial antigens (e.g., bacterial, viral, parasitic or fungal antigens), cancer or tumor-associated antigens, and/or self antigens. In many embodiments, a suitable antibody is one that recognizes and binds to an antigen present on or in a cell.

The IRM moiety of an IRM conjugate may be, or be derived from, any suitable IRM compound. Suitable IRM compounds include small organic molecules, i.e., molecules having a molecular weight of less than about 1000 Daltons, although in some embodiments a suitable IRM compound may have a molecular weight of less than about 700 Daltons. In certain cases a suitable IRM compound may have a molecular weight from about 500 Daltons to about 700 Daltons, while in other embodiments, a suitable IRM compound may have a molecular weight from about 250 to about 500 Daltons.

Suitable IRMs include compounds such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; U.S. Patent Publication Nos. 2004/0091491; 2004/0147543; 2004/0176367; and 2006/0100229; and International Publication Nos. WO2005/18551, WO2005/18556, WO2005/20999, WO2005/032484, WO2005/048933, WO2005/048945, WO2005/051317, WO2005/051324, WO2005/066169, WO2005/066170, WO2005/066172, WO2005/076783, WO2005/079195, WO2005/094531, WO2005/123079, WO2005/123080, WO2006/009826, WO2006/009832, WO2006/026760, WO2006/028545, WO2006/028962, WO2006/029115, WO2006/038923, WO2006/065280, WO2006/074003, WO2006/083440, WO2006/086449, WO2006/086633, WO2006/086634, WO2006/091394, WO2006/091567, WO2006/091568, WO2006/091647, WO2006/093514, WO2006/098852, WO2006/107771, WO2006/107851, and WO2006/107853.

Additional examples of small molecule IRMs include certain purine derivatives (such as those described in U.S. Pat. Nos. 6,376,501, and 6,028,076), certain imidazoquinoline amide derivatives (such as those described in U.S. Pat. No.

6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO2002/08905), certain 3-β-D-ribofuranosylthiazolo[4,5-d]pyrimidine derivatives (such as those described in U.S. Publication No. 2003/0199461), and certain small molecule immunopotentiator compounds such as those described, for example, in US2005/0136065.

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116, 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO2000/75304. Still other IRM nucleotide sequences include guanosine- and uridine-rich single-stranded RNA (ssRNA) such as those described, for example, in Heil et al., Science, vol. 303, pp. 1526-1529, Mar. 5, 2004.

Other IRMs include biological molecules such as aminoalkyl glucosaminide phosphates (AGPs) and are described, for example, in U.S. Pat. Nos. 6,113,918; 6,303,347; 6,525,028; and 6,649,172.

In some embodiments of the present invention, a suitable IRM compound may be an agonist of at least one TLR such as, for example, TLR7 or TLR8. The IRM may also in some cases be an agonist of TLR 9.

In some embodiments of the present invention, a suitable IRM compound may include a 2-aminopyridine fused to a five membered nitrogen-containing heterocyclic ring, or a 4-aminopyrimidine fused to a five membered nitrogen-containing heterocyclic ring.

Suitable IRM compounds include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

In certain embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, a hydroxylamine substituted imidazoquinoline amine, an oxime substituted imidazoquinoline amine, a 6-, 7-, 8-, or 9-aryl, heteroaryl, aryloxy or arylalkyleneoxy substituted imidazoquinoline amine, or an imidazoquinoline diamine. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

Suitable IRM compounds also may include the purine derivatives, imidazoquinoline amide derivatives, benzimidazole derivatives, adenine derivatives, aminoalkyl glucosaminide phosphates, small molecule immuno-potentiator compounds, and oligonucleotide sequences described above. In some embodiments, the IRM compound may be a compound identified as an agonist of one or more TLRs.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

The IRM conjugate may be provided in any formulation suitable for administration to a subject. Suitable types of formulations are described, for example, in U.S. Pat. No. 5,238,944; U.S. Pat. No. 5,939,090; U.S. Pat. No. 6,245,776; European Patent No. EP 0 394 026; and U.S. Patent Publication No. 2003/0199538. The conjugate may be provided in any suitable form including but not limited to a solution, a suspension, an emulsion, or any form of mixture. The conjugate may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including but not limited to adjuvants, skin penetration enhancers, colorants, fragrances, flavorings, moisturizers, thickeners, and the like.

A formulation containing the IRM conjugate may be administered in any suitable manner such as, for example, non-parenterally or parenterally. As used herein, non-parenterally refers to administration through the digestive tract, including by oral ingestion. Parenterally refers to administration other than through the digestive tract such as, for example, intravenously, intramuscularly, transdermally, subcutaneously, transmucosally (e.g., by inhalation), or topically.

The composition of a formulation suitable for practicing the invention will vary according to factors known in the art including but not limited to the physical and chemical nature of the conjugate (e.g., the IRM moiety and/or the second moiety), the nature of the carrier, the intended dosing regimen, the state of the subject's immune system (e.g., suppressed, compromised, stimulated), the method of administering the IRM conjugate, and the species to which the formulation is being administered. Accordingly, it is not practical to set forth generally the composition of a formulation that includes an IRM conjugate that is effective for all possible applications of the conjugate. Those of ordinary skill in the art, however, can readily determine an appropriate formulation with due consideration of such factors.

In some embodiments, the methods of the present invention include administering an IRM conjugate of the invention to a subject in a formulation of, for example, from about typically 0.0001% to about 20% (unless otherwise indicated, all percentages provided herein are weight/weight with respect to the total formulation) to the subject, although in some embodiments the IRM conjugate may be administered using a formulation that provides the conjugate in a concentration outside of this range. In certain embodiments, the method includes administering to a subject a formulation that includes from about 0.01% to about 1% of the IRM conjugate, for example, a formulation that includes about 0.1% to about 0.5% IRM conjugate.

The precise amount of IRM conjugate effective for use for a particular application will vary according to factors known in the art including but not limited to the physical and chemical nature of the IRM conjugate (e.g., the IRM moiety and/or the second moiety), the nature of the carrier, the intended dosing regimen, the state of the subject's immune system (e.g., suppressed, compromised, stimulated), the method of administering the IRM conjugate, and the species to which the formulation is being administered. Accordingly, it is not practical to set forth generally the amount that constitutes an amount of IRM conjugate effective for all possible applications. Those of ordinary skill in the art, however, can readily determine the appropriate amount with due consideration of such factors.

In some embodiments, the methods of the present invention include administering sufficient IRM conjugate to provide a dose of, for example, from about 100 ng/kg to about 50 mg/kg to the subject, although in some embodiments the methods may be performed by administering IRM conjugate in a dose outside this range. In some of these embodiments, the method includes administering sufficient IRM conjugate to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{0.725}$)×0.007184.

In some embodiments, the methods of the present invention may include administering sufficient IRM conjugate to provide a dose of, for example, from about 0.01 $mg/m^2$ to about 10 $mg/m^2$.

The dosing regimen may depend at least in part on many factors known in the art including but not limited to the physical and chemical nature of the IRM conjugate (e.g., the IRM moiety and/or the second moiety), the nature of the carrier, the amount of IRM being administered, the state of the subject's immune system (e.g., suppressed, compromised, stimulated), the method of administering the IRM conjugate, and the species to which the formulation is being administered. Accordingly it is not practical to set forth generally the dosing regimen effective for all possible applications. Those of ordinary skill in the art, however, can readily determine an appropriate dosing regimen with due consideration of such factors.

In some embodiments of the invention, the IRM conjugate may be administered, for example, from a single dose to multiple doses per week, although in some embodiments the methods of the present invention may be performed by administering the IRM conjugate at a frequency outside this range. In certain embodiments, the IRM conjugate may be administered from about once per month to about five times per week. In one particular embodiment, the IRM conjugate is administered once per week.

Conditions that may be treated by administering an IRM conjugate include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or *molluscum contagiosum*), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma,*

*Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, breast cancer, lung cancer, prostate cancer, colon cancer, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

IRM conjugates also may be useful to individuals having compromised immune function. For example, certain conjugates may be used for treating the opportunistic infections and tumors that occur after suppression of cell mediated immunity in, for example, transplant patients, cancer patients and HIV patients.

As noted above, the linker by which the IRM moiety and the second moiety are attached does not depend upon UV irradiation to form the linking covalent bond. In some embodiments, the covalent link includes a disulfide linkage, a thioether linkage, a hydrazone linkage, an oxime linkage, an amide linkage, a urea linkage, a thiourea linkage, a carbamate linkage, a hydrazine linkage, a hydroxylamine linkage, or a nitrone linkage. Of these, the hydrazine and hydroxylamine linkages are the reduced forms of the hydrazone and oxime linkages, respectively.

The methods of the present invention may be performed on any suitable subject. Suitable subjects include but are not limited to animals such as but not limited to humans, non-human primates, rodents, dogs, cats, horses, pigs, sheep, goats, or cows.

In another aspect, the present invention also provides a method of making an IRM conjugate. Generally, the method includes covalently attaching a first linker having a first functional group to an IRM compound having immunomodulatory activity, at a site on the IRM compound selected to preserve at least a portion of the immunomodulatory activity of the IRM compound, thereby forming an IRM moiety; and allowing the IRM moiety to react with a second moiety having biological activity and a second functional group by forming a covalent bond between the first functional group and the second functional group, thereby forming an IRM conjugate that possesses IRM activity and the biological activity of the second moiety.

In some cases, the second active moiety may be formed by reacting a compound having biological activity (e.g., antigenic and/or targeting activity) with a second linker at a site on the compound selected to preserve at least a portion of the compound's biological activity.

In other cases, the second active moiety may not require a linker. For example, the compound providing the biological activity of the second moiety may possess a functional group that can form a covalent bond with the first functional group without requiring UV irradiation while preserving at least a portion of the biological activity of the compound. Alternatively, such a second functional group may be easily generated, in some cases, by a chemical reaction such as, for example, reduction of a disulfide bond in a protein or oxidation of a carbohydrate on a glycoprotein.

In some embodiments employing linkers, a linker may be branched so that a moiety may include multiple compounds. For example, if the first linker is branched, multiple IRM compounds may be covalently attached to the first linker, thereby providing an IRM moiety with multiple IRMs. When multiple IRMs are included in the IRM moiety, the IRMs attached to the linker may be the same compound or different compounds.

Similarly, if the second linker is branched, multiple compounds may be attached to the second linker, providing the possibility of loading the second moiety with more than one biological activity. For example, the second linker may include at least one compound that provides antigenic activity and at least one compound that provides targeting activity. Alternatively, the second moiety may include different compounds, each of which provides different targeting activity—i.e., one compound may provide dendritic cell targeting activity and another compound may provide anti-tumor targeting activity, thereby providing delivery of IRM and dendritic cell to the vicinity of a tumor. Finally, the second moiety may be designed to include at least two different compounds that provide different antigenic activity. This may provide two (or more) distinct ways for the immune response to be directed toward a target having multiple target-specific antigenic character.

Of course, both the first and the second linker may be branched, permitting the loading of multiple IRMs and multiple second compounds within a single IRM conjugate. Moreover, the use of branched linkers may be combined with the use of solid supports to further expand the possible combinations of activities that may be included in a single IRM conjugate.

In still other cases, the second moiety may include a solid support that includes the second functional group, which is covalently attached to the compound having biological activity, either directly or through a linker. Suitable solid supports are described, for example, in U.S. Patent Publication No. 2004/0258698. In one particular embodiment, a suitable solid support is a gold nanoparticle. A solid support may include a plurality of functional groups, thereby permitting the attachment of a plurality of IRM moieties and/or multiple compounds having biological activity.

When a plurality of IRM moieties is attached to a solid support, the IRM moieties may be derived from the same IRM compound or from different IRM compounds. Likewise, when a plurality of compounds having biological activity is attached to a solid support, the compounds may be the same or different, offering the opportunity to design a conjugate having more than one biological activity: for example, at least two different antigenic activities, at least two different targeting activities, and/or a mixture of antigenic and targeting activities.

Preparation of Conjugates

Conjugates of the invention can be prepared using the general method illustrated in Reaction Scheme I, wherein IRM and second active moiety (SAM) are as described above, p is an integer from 1 to 20, $FG_A$ and $FG_B$ are functional groups described in greater detail below and specifically exemplified in Table A below, and Linker A, Linker B, and Linker C are defined below.

TABLE A

| Linkage | Bond | FG$_A$ | FG$_B$ |
| --- | --- | --- | --- |
| 1a | disulfide | —SH | pyridyl disulfide |
| 1b | disulfide | pyridyl disulfide | —SH |
| 2a | thiosuccinimide | —SH | maleimide |
| 2b | thiosuccinimide | maleimide | —SH |
| 3a | thioacetamide | —SH | LG-CH$_2$-C(O)NH— |
| 3b | thioacetamide | LG-CH$_2$-C(O)NH— | —SH |
| 4a | acyl hydrazone | H$_2$N-NH-C(O)— | R-C(O)— |
| 4b | acyl hydrazone | R-C(O)— | H$_2$N-NH-C(O)— |
| 5a | hydrazone | H$_2$N-NH— | R-C(O)— |
| 5b | hydrazone | R-C(O)— | H$_2$N-NH— |
| 6a | oxime | H$_2$N-O— | R-C(O)— |
| 6b | oxime | R-C(O)— | H$_2$N-O— |

TABLE A-continued

| Linkage | Bond | FG$_A$ | FG$_B$ |
|---|---|---|---|
| 7 | -C(=O)-NH- | -C(=O)-AAG | H$_2$N- |
| 8 | -NH-C(=O)-NH- | N=C=O | H$_2$N- |
| 9 | -NH-C(=S)-NH- | N=C=S | H$_2$N- |
| 10 | -O-C(=O)-NH- | -O-C(=O)-G | H$_2$N- |
| *11 | -CHR-NH-NH-C(=O)- | | |
| *12 | -CHR-NH-NH- | | |
| *13 | -CHR-NH-O- | | |
| 14 | -C(R)=N$^+$(O$^-$)- | HO-NH- | R-C(=O)- |
| 15 | -C(R)=N$^+$(O$^-$)- | R-C(=O)- | HO-NH- |

LG is a leaving group selected from Cl, Br, I, O-mesyl, and O-Tosyl.

AAG is an acid activating group selected from an EDC activated acid; NHS, sNHS, 4-nitrophenyl, chloride, bromide, anhydride or mixed anhydride, pentafluorophenyl ester, and tetrafluorophenyl ester.

G is selected from Cl, O—CH(Cl)CCl$_3$, O-(4-nitrophenyl), NHS, and imidazole.

*Linkages 11-13 obtained by reduction of linkages 4-6.

R is hydrogen, alkyl, aryl, or arylalkylenyl.

Linker A is an organic moiety that links the IRM with functional group $FG_A$. Suitable linkers include divalent organic moieties of the formulas —X—, —X—Y—X—, —Z—X—, and —Z—X—Y—X— wherein X, Y, and Z are as defined below. Examples of such linkers include —$C_{1-10}$-alkylene-, —O—($C_{1-8}$alkylene)-arylene, —$C_{1-10}$alkylene-arylene-, arylene-$C_{1-10}$alkylene-, —$C_3$-$C_8$-heterocyclene-, —$C_{1-10}$alkylene-$C_3$-$C_8$-heterocyclene-, and —$C_3$-$C_8$-heterocyclene-$C_{1-10}$-alkylene-. Other suitable linkers include —$(CH_2CH_2O)_q$— and —$(CH_2CH_2O)_q$—$CH_2$— wherein q is an integer from 1 to 10. Suitable linkers also include those discussed in greater detail in the Reaction Schemes below and those specifically exemplified in the EXAMPLES below.

Linker B is an organic moiety that links the SAM with functional group $FG_B$. Suitable linkers include, but are not limited to, divalent organic moieties of the formulas —X—, —X—Y—X—, —Z—X—, and —Z—X—Y—X— wherein X, Y, and Z are as defined below. Examples of such linkers include —$C_{1-10}$-alkylene-, —O—($C_{1-8}$alkylene)-arylene, —$C_{1-10}$alkylene-arylene-, arylene-$C_{1-10}$alkylene-, —$C_3$-$C_8$-heterocyclene-, —$C_{1-10}$alkylene-$C_3$-$C_8$-heterocyclene-, and —$C_3$-$C_8$-heterocyclene-$C_{1-10}$-alkylene-. Other suitable linkers include —$(CH_2CH_2O)_q$— and —$(CH_2CH_2O)_q$—$CH_2$— wherein q is an integer from 1 to 10. Suitable linkers also include those discussed in greater detail in the Reaction Schemes below and those specifically exemplified in the EXAMPLES below.

Linker C is an organic moiety that links one or more IRMs with the SAM. Linker C includes the linkage formed when $FG_A$ and $FG_B$ react with each other. Examples of such linkages include those in Table A above. In some embodiments, the linkage can be cleaved in vivo to release the IRM. Examples of such linkages include, but are not limited to, disulfide linkages and hydrazone linkages. The structure of the Linker C is determined by the structures of Linker A and Linker B and by the particular $FG_A$ and $FG_B$ groups attached to the IRM or the SAM.

In step (1) of Reaction Scheme I, a second active moiety (SAM) is modified to provide a functionalized moiety of Formula II using conventional methods including those described in the EXAMPLES below.

Functionalized moieties of Formula II can be prepared using a heterobifunctional crosslinker. The general definition of a heterobifunctional crosslinker is as follows " . . . a heterobifunctional cross-linking agent includes two different reactive groups at either end, and an organic cross-bridge of various length and composition." (Hermanson, G. (1996), *Bioconjugate Techniques*, Academic Press, Chapter 5 "Heterobifunctional Cross-Linkers", page 229). Useful functional groups often found on SAMs include, but are not limited to, amines (—$NH_2$), thiols (—SH), and aldehydes (—CHO), which can be derivatized with heterobifunctional crosslinkers that contain, respectively, amine reactive groups, thiol reactive groups, and aldehyde reactive groups. The other reactive group on the heterobifunctional crosslinker is chosen such that it provides the desired functional group $FG_B$ in a functionalized moiety of Formula II. Many heterobifunctional cross-linkers are known (Hermanson, G. (1996), *Bioconjugate Techniques*, Academic Press, Chapter 5 "Heterobifunctional Cross-Linkers", pages 229-285) and many are commercially available (Pierce Biotechnology, Inc. of Rockford, Ill. and other suppliers). In addition, heterobifunctional crosslinkers can also be synthesized using conventional methods.

Functional groups on a heterobifunctional crosslinker that can react with amines on the SAM include, but are not limited to, any functional group $FG_A$ that can react with an amine as shown in Table A. Preferred functional groups include activated carboxylic acids such N-hydroxysuccinimide esters or sulfo-N-hydroxysuccinimide esters, isocyanates, and thioisocyanates. Examples of useful heterobifunctional crosslinkers that can react with amines and provide $FG_B$ as a maleimide are the following: sulfo-N-succinimidyl 4-(maleimidomethyl)cyclohexane-1-carboxylate, sodium salt (Sulfo SMCC)

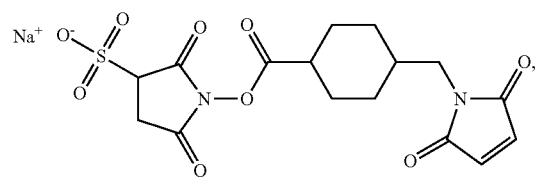 [SMILES: [Na+] ; O=C(ON1C(=O)CC(S(=O)(=O)[O-])C1=O)C1CCC(CN2C(=O)C=CC2=O)CC1]

N-(γ-maleimidobutyryloxy)sulfosuccinimide ester (Sulfo-GMBS)

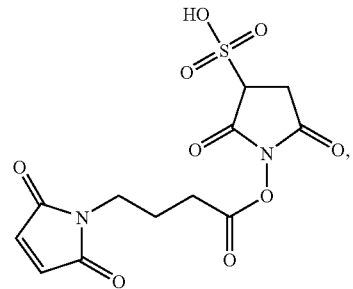

succinimidyl-[(N-maleimidopropionamido)-tetraethyleneglycol]ester (NHS-$PEO_4$-Maleimide)

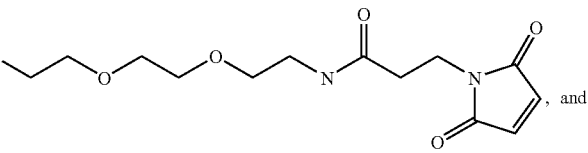

, and succinimidyl-[(N-maleimidopropionamido)-octaethyleneglycol]ester, (NHS-$PEO_8$-Maleimide)

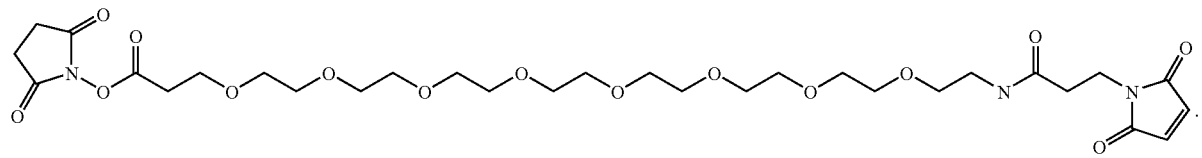 [SMILES: O=C(CCN1C(=O)C=CC1=O)NCCOCCOCCOCCOCCOCCOCCOCCOCCC(=O)ON1C(=O)CCC1=O]

An example of a useful heterobifunctional crosslinker that can react with an amine and provide $FG_B$ as an bromo acetyl group is N-succinimidyl 3-(bromoacetamido)propionate (SBAP),

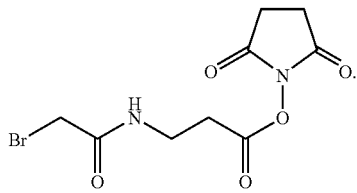 [SMILES: O=C(CBr)NCCC(=O)ON1C(=O)CCC1=O]

An example of a useful heterobifunctional crosslinker that can react with an amine and provide $FG_B$ as a 2-pyridyl disulfide is 4-succinimidyloxycarbonyl-methyl-α-(2-pyridyldithio)toluene (SMPT),

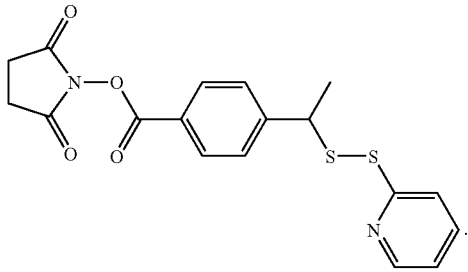 [SMILES: CC(SSc1ccccn1)c1ccc(C(=O)ON2C(=O)CCC2=O)cc1]

In general, when the SAM contains a thiol group, the SAM may be treated with a reagent such as N-ethylmaleimide prior to treatment with a heterobifunctional crosslinker that installs $FG_B$ as a thiol reactive group. This prevents dimerization/oligomerization of the SAM of Formula II.

In addition, a useful reagent that can react with amines in a SAM to install a thiol as $FG_B$ in a functionalized moiety of Formula II is Traut's reagent (2-iminothiolane hydrochloride),

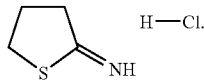

In some embodiments the SAM may contain a thiol that can react with a heterobifunctional crosslinker in step (1) of Reaction Scheme I to provide a functionalized moiety of Formula II. Heterobifunctional crosslinkers that are reactive toward thiols may contain, but are not limited to, any functional group $FG_A$ that can react with a thiol as shown in Table A. Preferred functional groups include activated disulfides such as a 2-pyridyl disulfide and a methyl sulfonyl disulfide, maleimides, and bromo or iodo acetyl groups. Some examples of useful heterobifunctional cross-linkers that can react with thiols and provide $FG_B$ as a hydrazide are [N-ε-maleimidocaproic acid]hydrazide (EMCH)

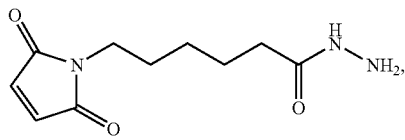

[N-ε-maleimidoundecanoic acid]hydrazide (KMUH),

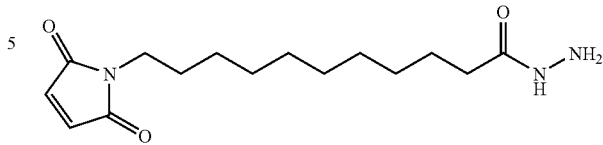

3-(2-pyridyldithio)propionyl hydrazide (PDPH),

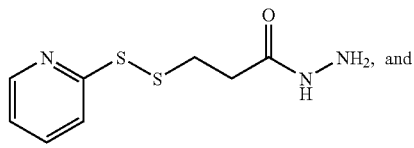

4-(maleimidomethyl)cyclohexane-1-carboxyl-hydrazide, trifluoracetic acid (SMCC-Hydrazide, TFA),

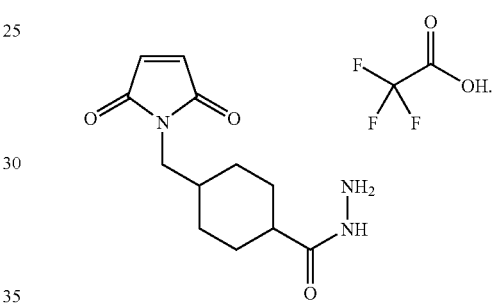

In some embodiments, the SAM will contain an aldehyde that can react with a heterobifunctional crosslinker in step (1) of Reaction Scheme I to provide a functionalized moiety of Formula II. Functional groups on a heterobifunctional crosslinker that can react with an aldehyde on the SAM include, but are not limited to, any functional group $FG_A$ that can react with an aldehyde as shown in Table A. Useful functional groups include hydrazines (—NHNH$_2$), hydrazides (—C(O) NHNH$_2$), amines (—NH$_2$), hydroxyl amines (—NHOH), and O— substituted hydroxylamines (—O—NH$_2$). Examples of useful heterobifunctional crosslinkers that can react with aldehydes and provide $FG_B$ as a maleimide include EMCH, KMUH, and SMCC-Hydrazide. A useful heterobifunctional crosslinker that can react with aldehydes and provide $FG_B$ as a 2-pyridyl disulfide is PDPH. A functionalized moiety of Formula II that contains $FG_B$ as a 2-pyridyl disulfide can be reduced using known methods to provide $FG_B$ as a thiol.

Although not illustrated, in some embodiments the SAM may be used without the incorporation of Linker B. For example, a SAM that contains a functional group $FG_B$, can react with a functionalized IRM of Formula III to form a IRM-SAM Conjugate of Formula I. Useful functional groups $FG_B$ on the SAM include, but are not limited to, amines (—NH$_2$), thiols (—SH), and aldehydes (—CHO). When the SAM is a protein, it may contain cysteine or lysine amino acid residues that contain, respectively, thiols and amines. In some instances, useful functional groups $FG_B$ may be generated easily on the SAM. For example, carbohydrate residues on a glycoprotein can be oxidized using sodium periodate to form reactive aldehydes (Hermanson, G. (1996), *Bioconjugate Techniques*, Academic Press, p. 114). Furthermore, disulfide bonds in a protein can be reduced using a variety of reducing agents (Hermanson, G. (1996), *Bioconjugate Techniques*, Academic Press, p. 76) to form thiols.

In step (2) of Reaction Scheme I, an IRM is modified to provide a functionalized IRM of Formula III.

Functionalized IRMs of Formula III can be prepared using a heterobifunctional crosslinker by employing a similar strategy to that described in step (1) above. Useful functional groups on the IRM that may be modified by a heterobifunctional crosslinker include, but are not limited to, amines, thiols, ketones, hydrazines (—NHNH$_2$), hydroxylamines (—NHOH), and O-alkylhydroxylamines (—O—NH$_2$). Examples of useful heterobifunctional crosslinkers that can react with an amine in the IRM include N-succinimidyl 3-(2-pyridyldithio)propionate, N-succinimidyl-3-maleimidopropionate, and the reagent 2-iminothiolane hydrochloride, which yield functionalized IRMs of Formula III where FG$_A$ is a maleimide, pyridyldisulfide, and thiol, respectively.

Although not illustrated, in some embodiments the IRM may be used without the incorporation of Linker A. For example, an IRM that contains a functional group FG$_A$ can react with a functionalized moiety of Formula II to form an IRM-SAM conjugate of Formula I. Preferred functional groups FG$_A$ in the IRM include, but are not limited to, amines, ketones, thiols (—SH), hydrazides (—C(O)NHNH$_2$), hydrazines (—NHNH$_2$), hydroxylamines (—NHOH), and O-alkylhydroxylamines (—O—NH$_2$).

As described in greater detail below, functionalized IRMs of Formula III may be synthesized by means other than employing a heterobifunctional crosslinker. These alternative methods can provide linkers that cannot be obtained using commercially available heterobifunctional crosslinkers and may provide IRM-SAM conjugates having enhanced physical and/or biological properties as compared to those conjugates prepared using the commercially available heterobifunctional crosslinkers. The linker's length, rigidity or flexibility, and hydrophobicity or hydrophilicity can be optimized for each IRM-SAM conjugate of Formula I. Furthermore, the linker can be designed and synthesized to include a branching point so that multiple IRMs may be attached to a single linker. Examples of such linkers include, but are not limited to, those described in the literature (King et. al, *J. Med. Chem.*, 2002, 45, 4336). Finally, the linker can be designed and synthesized such that the IRM is released from the IRM-SAM Conjugate of Formula I in vivo. For example, the linker may contain labile linkages that include, but are not limited to, a disulfide bond, a hydrazone moiety, or the amide bond of a peptide unit used with or without a self-immolative spacer, such as those described in the literature (Toki, B. E. et al. *J. Org. Chem.*, 2002, 67, 1866-1872; Jeffrey, S. C. et al.; *J. Med. Chem.*, 2005, 48, 1344-1358; Sun, M. M. C. et al., *Bioconjugate Chem.* 2005, 16, 1282-1290) and International Publication Nos. WO2005/082023 and WO2004/0101957.

In step (3) of Reaction Scheme I, a functionalized moiety of Formula II is reacted with a functionalized IRM of Formula III to provide an IRM-SAM conjugate of Formula I using conventional methods including those described in the EXAMPLES below. For example, the reaction can be carried out by adding a solution of the functionalized IRM of Formula III in a suitable solvent such as dimethyl sulfoxide (DMSO) or N,N-dimethylformamide to a solution of a functionalized moiety of Formula II in a suitable buffer such as phosphate buffered saline (PBS). The reaction can be carried out at ambient temperature. The resulting IRM-SAM conjugate of Formula I can be purified using conventional methods such as, for example, size exclusion chromatography.

The functionalized moiety of Formula II and the functionalized IRM of Formula III are selected such that functional groups FG$_A$ and FG$_B$ react with each other to form a new covalent bond in the IRM-SAM conjugate of Formula I.

In some embodiments, FG$_A$ is an electrophilic group that is reactive to FG$_B$, which is a nucleophilic group. Useful electrophilic groups in include, but are not limited to, Michael acceptors such as maleimides, vinylsulfones, and acrylic acid derivatives; activated disulfides such as pyridyldisulfide and methyl sulfonyl disulfide; activated carboxylic acids such as N-hydroxysuccinimide ester, sulfo-N-hydroxysuccinimide ester, 4-nitrophenyl ester, acid chloride, acid bromide, acid anhydride, pentafluorophenyl ester, and tetrafluorophenyl ester; haloacetyl groups such as iodo-, bromo-, and chloroacetyl; activated carbonates such as succinimidyl carbonate, chloroformate (—OC(O)Cl), and carbonates of the formula —OC(O)—O—CH(Cl)CCl$_3$ and —OC(O)-(4-nitrophenyl); isocyanates; thioisocyanates; aldehydes; and ketones. Preferred FG$_A$ groups include, but are not limited to, maleimide, pyridyldisulfide, and the activated acid groups described above. Useful nucleophilic groups in include, but are not limited to, thiols (—SH), hydrazines (—NHNH$_2$), hydrazides (—C(O)NHNH$_2$), amines (—NH$_2$), hydroxylamines (—NHOH), and O-alkyl-hydroxylamines (—O—NH$_2$). The preferred FG$_B$ groups include, but are not limited to, thiols, amines, hydrazines, and hydrazides.

In some embodiments, FG$_A$ is a nucleophilic group that is reactive to FG$_B$, which is an electrophilic group. Preferred nucleophilic FG$_A$s include, but are not limited to, sulfhydryl and hydrazide groups. Preferred electrophilic in FG$_B$s include, but are not limited to, maleimide, pyridyldisulfide, aldehyde groups.

Reaction Scheme I

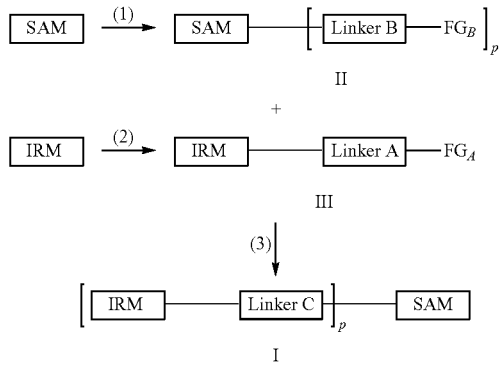

In some embodiments, conjugates of the invention can be prepared using the general method illustrated in Reaction Scheme II, wherein IRM, SAM, FG$_A$, FG$_B$, Linker A, Linker B, Linker C, and p are as defined above and R$_A$ and R$_B$ are each independently selected from the group consisting of:
hydrogen,
halogen,
alkyl,
alkenyl,
alkoxy,
alkylthio, and
—N(R$_9$)$_2$;

or when taken together, $R_A$ and $R_B$ form a fused aryl ring or heteroaryl ring containing one heteroatom selected from the group consisting of N and S wherein the aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—$N(R_9)_2$;

$R_2$ is selected from the group consisting of:
—$R_4$,
—X—$R_4$,
—X—Y—$R_4$, and
—X—$R_5$;

$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

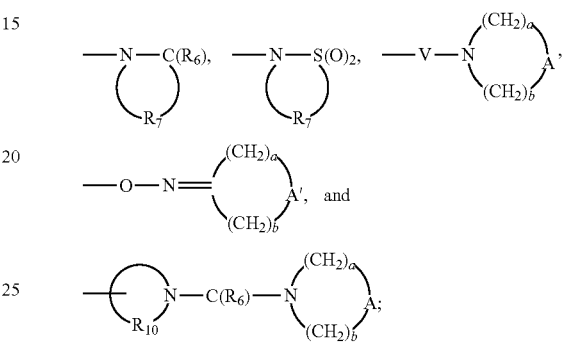

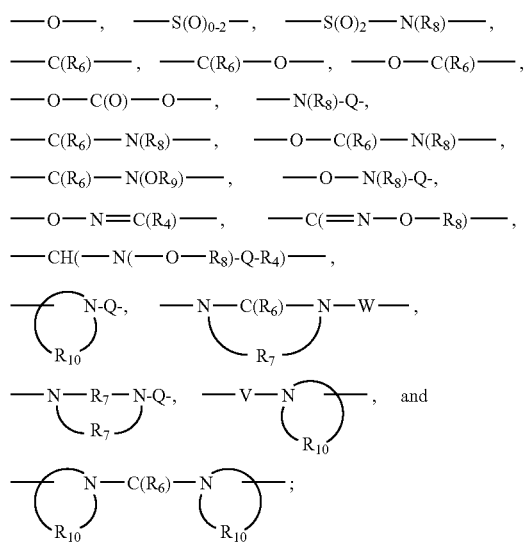

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of $R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —C(O)—, —$S(O)_{0-2}$—, and —$N(R_4)$—;

A' is selected from the group consisting of —O—, —$S(O)_{0-2}$—, —N(-Q-$R_4$)—, and —$CH_2$—;

Q is selected from the group consisting of a bond, —$C(R_6)$—, —$C(R_6)$—$C(R_6)$—, —$S(O)_2$—, —$C(R_6)$—N($R_8$)—W—, —$S(O)_2$—N($R_8$)—, —$C(R_6)$—O—, —$C(R_6)$—S—, and —$C(R_6)$—N($OR_9$)—;

V is selected from the group consisting of —$C(R_6)$—, —O—$C(R_6)$—, —N($R_8$)—$C(R_6)$—, and —$S(O)_2$—;

W is selected from the group consisting of a bond, —C(O)—, and —$S(O)_2$—; and a and b are independently integers from 1 to 6 with the proviso that a+b is ≤7.

In Reaction Scheme II, a functionalized IRM of Formula IIIa, which is a subgenus of Formula III, is reacted with a functionalized moiety of Formula II to provide an IRM-Sam conjugate of Formula Ia, which is a subgenus of Formula I. The reaction can be carried out as described for step (3) of Reaction Scheme I.

Functionalized IRMs of Formula IIIa can be prepared using the general methods described in step (2) of Reaction Scheme I and using the methods described in greater detail below.

Functionalized moieties of Formula II can be prepared as described in step (1) of Reaction Scheme I.

Reaction Scheme II

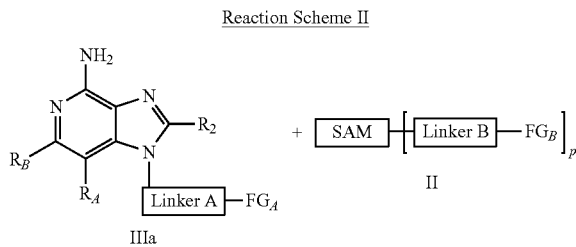

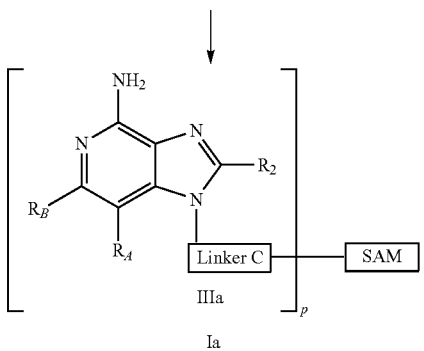

In some embodiments, conjugates of the invention can be prepared using the general method illustrated in Reaction Scheme III, wherein IRM, SAM, $FG_A$, $FG_B$, Linker A, Linker B, Linker C, p, and $R_2$ are as defined above and E is a carbon atom (imidazoquinolines) or a nitrogen atom (imidazonaphthyridines) and $R_1$ is selected from the group consisting of:
—$R_4$,
—X—$R_4$,
—X—Y—$R_4$,
—X—Y—X—Y—$R_4$, and
—X—$R_5$;
wherein X, Y, $R_4$, and $R_5$ are as defined above.

In Reaction Scheme III, a functionalized IRM of Formula IIIb, which is a subgenus of Formula III, is reacted with a functionalized moiety of Formula II to provide an IRM-Sam conjugate of Formula Ib, which is a subgenus of Formula I. The reaction can be carried out as described for step (3) of Reaction Scheme I.

Functionalized IRMs of Formula IIIb can be prepared using the general methods described in step (2) of Reaction Scheme I and using the methods described in greater detail below.

Functionalized moieties of Formula II can be prepared as described in step (1) of Reaction Scheme I.

Reaction Scheme III

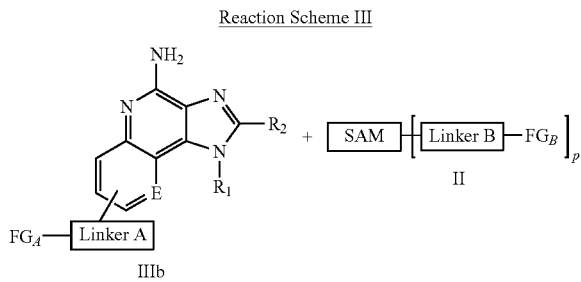

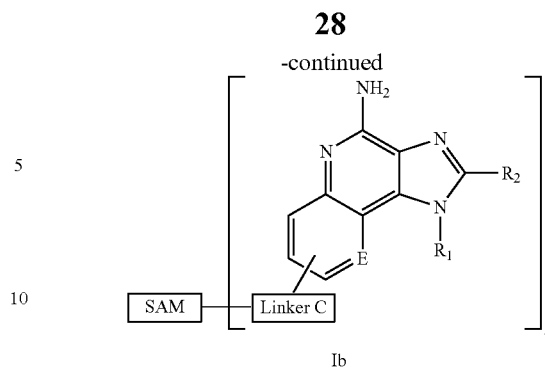

In some embodiments, conjugates of the invention can be prepared using the general method illustrated in Reaction Scheme IV, wherein IRM, SAM, $FG_A$, $FG_B$, Linker A, Linker B, Linker C, p, E, and $R_2$ are as defined above.

In Reaction Scheme IV, a functionalized IRM of Formula IIIc, which is a subgenus of Formula III, is reacted with a functionalized moiety of Formula II to provide an IRM-Sam conjugate of Formula Ic, which is a subgenus of Formula I. The reaction can be carried out as described for step (3) of Reaction Scheme I.

Functionalized IRMs of Formula IIIc can be prepared using the general methods described in step (2) of Reaction Scheme I and using the methods described in greater detail below.

Functionalized moieties of Formula II can be prepared as described in step (1) of Reaction Scheme I.

Reaction Scheme IV

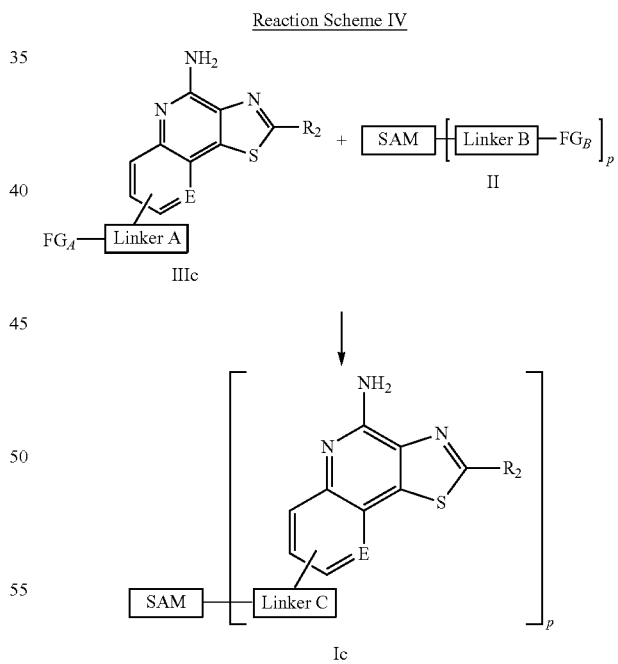

In some embodiments, functionalized IRMs can be prepared according to the method of Reaction Scheme V wherein $R_2$, $R_A$, $R_B$, $FG_A$, and X are as defined above and P is an amino protecting group such as a benzyloxycarbonyl (CBZ) or tert-butoxycarbonyl (BOC) group.

In step (1) of Reaction Scheme V, an IRM of Formula IV is reacted with a compound that contains both a carboxylic acid group and a suitably protected amino group, such as, for example, 6-[(tert-butoxycarbonyl)amino]hexanoic acid or 6-{[(benzyloxy)carbonyl]amino}hexanoic acid, which ultimately serves to increase the length of Linker C in an IRM-SAM conjugate of Formula Ia. The reaction can be carried out by adding a diamine of Formula IV, or the hydrochloric acid salt thereof, to a solution of the N-hydroxysuccinimide (NHS) or 1-hydroxybenzotriazole (HOBt) ester of 6-[(tert-butoxycarbonyl)amino]hexanoic acid or 6-{[(benzyloxy)carbonyl]amino}hexanoic acid. The NHS or HOBt ester is prepared by conventional methods such as, for example, by combining the acid, NHS or HOBt, and 1-(3-dimethylaminopropyl)-3-ethylcarbodiimide hydrochloride (EDC) in a suitable solvent such as N,N-dimethylformamide (DMF) at a sub-ambient temperature, such as 0° C. If the hydrochloride salt of a compound of Formula IV is used, an equivalent of a base such as triethylamine is added to the reaction mixture. The product of Formula V or a pharmaceutically acceptable salt thereof can be isolated using conventional methods. Many compounds of Formula IV are known; others can be prepared using known synthetic methods. See for example U.S. Pat. Nos. 6,069,149; 6,194,425; 6,756,382; 6,677,349; 6,541,485; 6,545,016; 6,660,747; 6,683,088; 6,656,938; and 6,797,718.

In step (2) of Reaction Scheme V, the amine protecting group of a compound of Formula V is removed to provide a diamine of Formula VI. When the amine protecting group is a tert-butoxycarbonyl (BOC) group, a compound of Formula V is treated either with trifluoroacetic acid in dichloromethane at ambient temperature or with hydrogen chloride in ethanol at an elevated temperature, such as the reflux temperature of the solvent. When the amine protecting group is a benzyloxycarbonyl (CBZ) group, a compound of Formula V is reduced with hydrogen in the presence of a conventional heterogeneous hydrogenation catalyst such as palladium on carbon or palladium hydroxide on carbon to provide a compound of Formula VI. The reaction can conveniently be carried out on a Parr apparatus in a suitable solvent such as ethanol. The product of Formula VI or a pharmaceutically acceptable salt thereof can be isolated using conventional methods.

In steps (3a) and (3b) of Reaction Scheme V, a compound of Formula VI is treated with a heterobifunctional crosslinker that is reactive toward amines, for example, a heterobifunctional cross linker containing a NHS ester. The heterobifunctional cross linker is chosen such that the resulting compound of Formula IIIe or IIId contains the desired functional group $FG_4$.

In step (3a) of Reaction Scheme V, a compound of Formula VI is reacted with the heterobifunctional crosslinker N-succinimidyl 3-(2-pyridyldithio)propionate. The reaction can be carried out in a suitable solvent such as tetrahydrofuran or DMF, or a mixture thereof. If the hydrochloride salt of a compound of Formula VI is used, the reaction is carried out in the presence of a tertiary amine such as triethylamine. The product of Formula IIIe, which is a subgenus of Formula III, or a pharmaceutically acceptable salt thereof, can be isolated using conventional methods.

In step (3b) of Reaction Scheme V, a compound of Formula VI is reacted with the heterobifunctional cross-linker N-succinimidyl-3-maleimidopropionate. The reaction can be carried out in a suitable solvent such dichloromethane. The product of Formula IIId, which is a subgenus of Formula III, or a pharmaceutically acceptable salt thereof, can be isolated using conventional methods.

Alternatively, as shown in step (3c) of Reaction Scheme V, in some embodiments, compounds of Formula IIIf can be synthesized directly, without extending the chain, from an amine of Formula IV. The reaction can be carried out using a variety of heterobifunctional cross-linkers and the general procedures described in steps (3a) and (3b) above. A compound of Formula IIIf or a pharmaceutically acceptable salt thereof can be isolated using conventional methods.

Reaction Scheme V

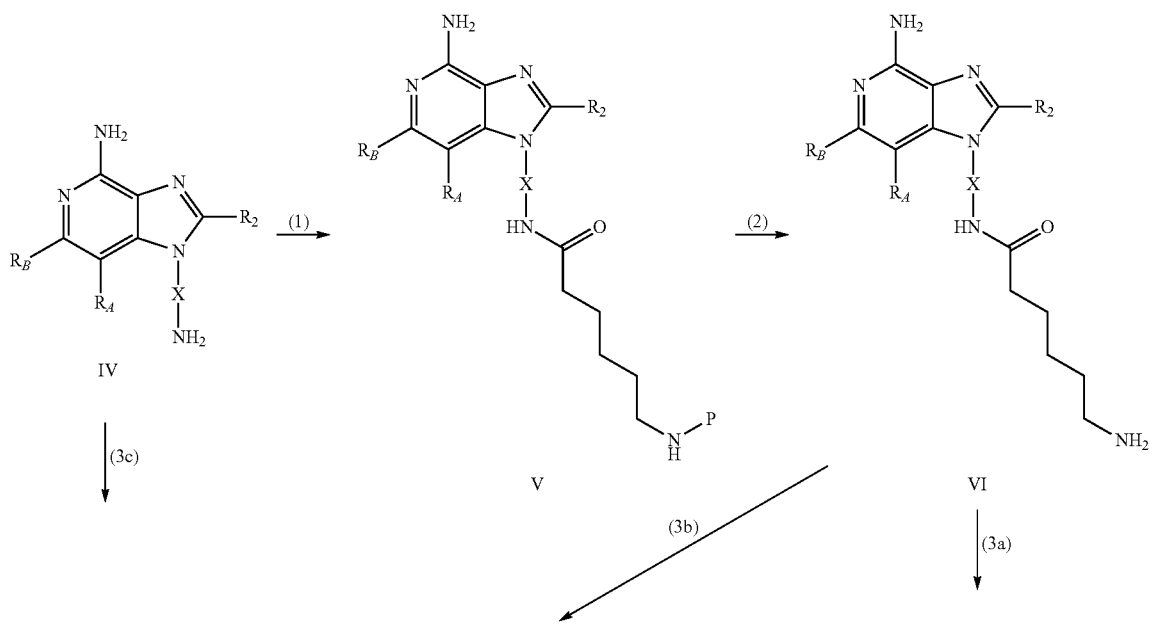

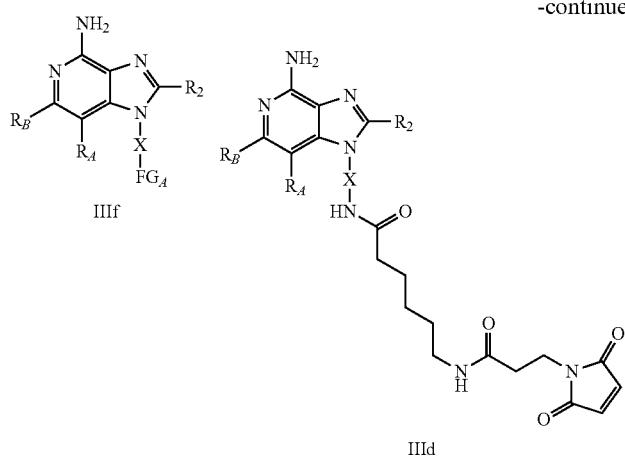

IIIf IIId IIIe

In some embodiments, functionalized IRMs can be prepared according to the method of Reaction Scheme VI wherein $R_2$, $R_A$, $R_B$, and X are as defined above.

In step (1) of Reaction Scheme VI, a compound of Formula VI is reacted with a symmetrical diacid that contains a disulfide group, for example 3,3'-dithiodipropionic acid, to form a disulfide dimer of Formula VII. The reaction can be carried out using the methods described for step (1) of Reaction Scheme V. The product of Formula VII, or a pharmaceutically acceptable salt thereof, can be isolated using conventional methods.

In step (2) of Reaction Scheme VI, the disulfide group in a dimer of Formula VII is reduced using conventional methods to provide a compound of Formula IIIg, which is a subgenus of Formula III. For example, the reduction can be carried out by treating a solution of a compound of Formula VII in methanol with tris(2-carboxyethyl)phosphine hydrochloride followed by the addition of aqueous sodium hydroxide. The reaction can be carried out at ambient temperature. The reduction of the disulfide bond can also be carried out using other conventional reducing agents such as tri-n-butylphosphine, sodium borohydride, or dithiothreitol. The product of Formula IIIg, or a pharmaceutically acceptable salt thereof, can be isolated using conventional methods.

Thiol substituted compounds of Formula IIIg can also be obtained by reduction of compounds of Formula IIIe using the same reduction methods.

Reaction Scheme VI

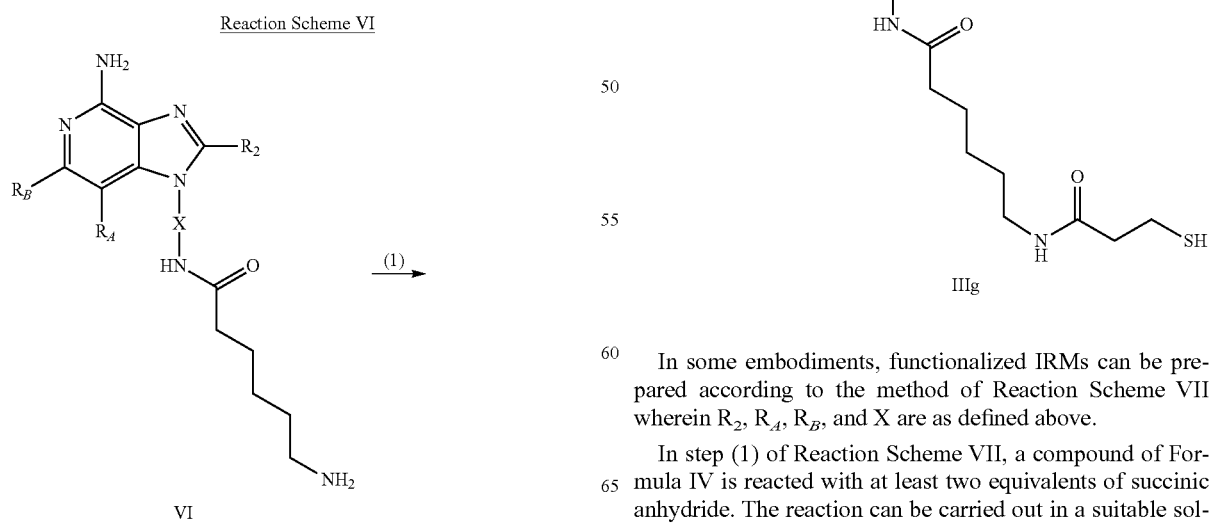

VI VII IIIg

In some embodiments, functionalized IRMs can be prepared according to the method of Reaction Scheme VII wherein $R_2$, $R_A$, $R_B$, and X are as defined above.

In step (1) of Reaction Scheme VII, a compound of Formula IV is reacted with at least two equivalents of succinic anhydride. The reaction can be carried out in a suitable solvent such as DMF at an elevated temperature such as 100° C.

The product of Formula VIII, or a pharmaceutically acceptable salt thereof, can be isolated using conventional methods.

In step (2) of Reaction Scheme VII, the acid group on a compound of Formula VIII is activated with a carbodiimide reagent, for example, 1-(3-dimethylaminopropyl)-3-ethyl-carbodiimide hydrochloride (EDC), in the presence of tert-butylcarbazate. The reaction can be carried out in a suitable solvent such as dichloromethane, optionally in the presence of a base such as triethylamine or a catalyst such as N,N-dimethylpyridin-4-amine (DMAP). The protecting group in the intermediate product can be removed by treatment with an excess of an amine such as, for example, ethylene diamine, in a suitable solvent such as dichloromethane to provide the product of Formula IX. Compounds of Formula IX, or a pharmaceutically acceptable salt thereof, can be isolated using conventional methods.

In step (3) of Reaction Scheme VII, the tert-butoxycarbonyl (BOC) group in a compound of Formula IX is removed under acidic conditions to provide a functionalized IRM of Formula IIIh, which is a subgenus of Formula III. The reaction can be carried out by treating a solution of a compound of Formula IX in a suitable solvent such as dichloromethane with an acid such as trifluoroacetic acid at ambient temperature. The product of Formula IIIh, or a pharmaceutically acceptable salt thereof, can be isolated using conventional methods.

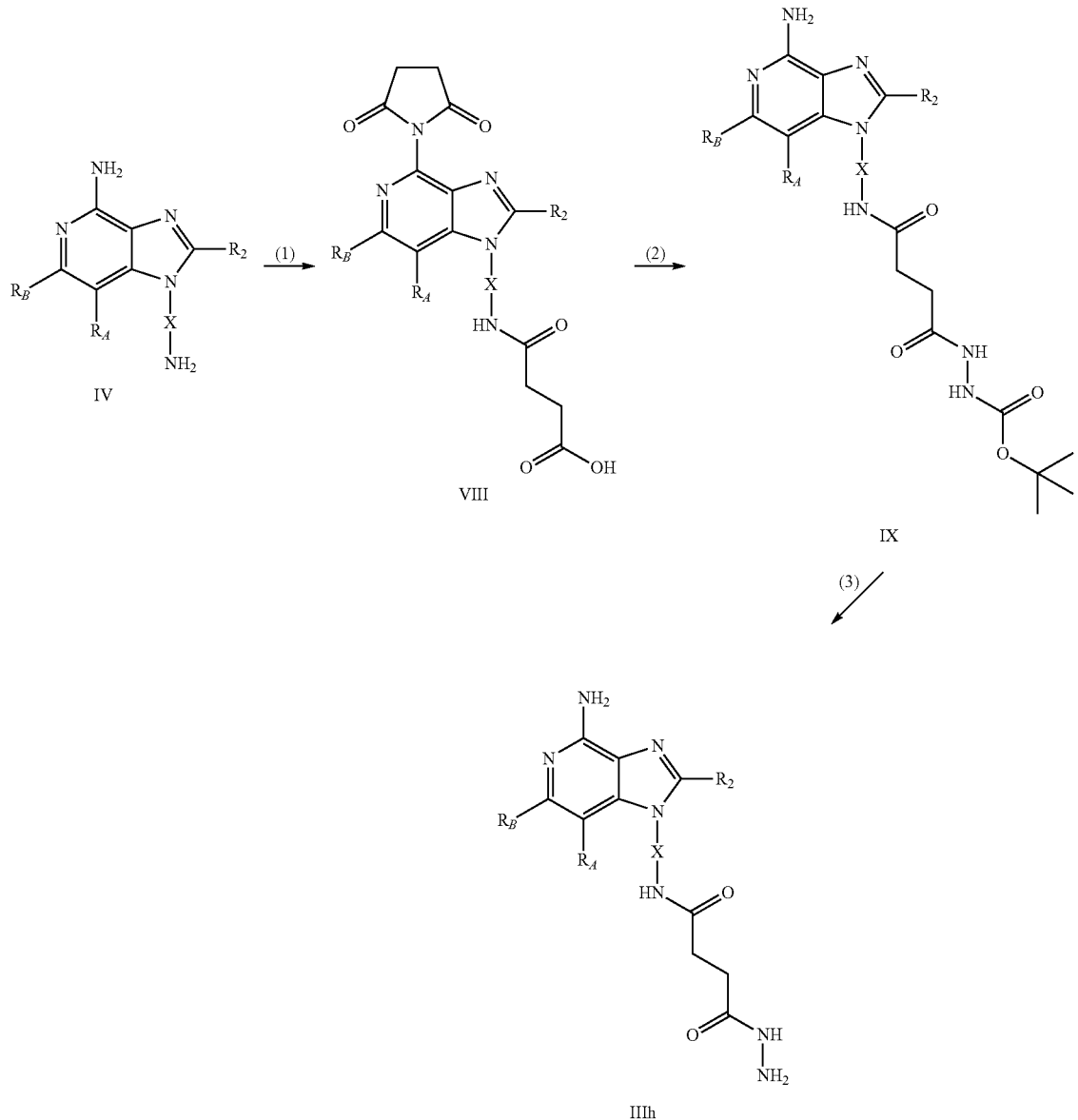

Reaction Scheme VII

In some embodiments, functionalized IRMs can be prepared according to the methods described in Reaction Schemes V, VI, and VII using compounds of Formulas X, XI, XII, XIII, or XIV wherein $R_1$, $R_2$, $R_A$, $R_B$, X, and Z are as described above, in lieu of a compound of Formula IV. In preferred embodiments, the —Z—X—$NH_2$ or —X—$NH_2$ groups are attached at the 7 position or the 8 position.

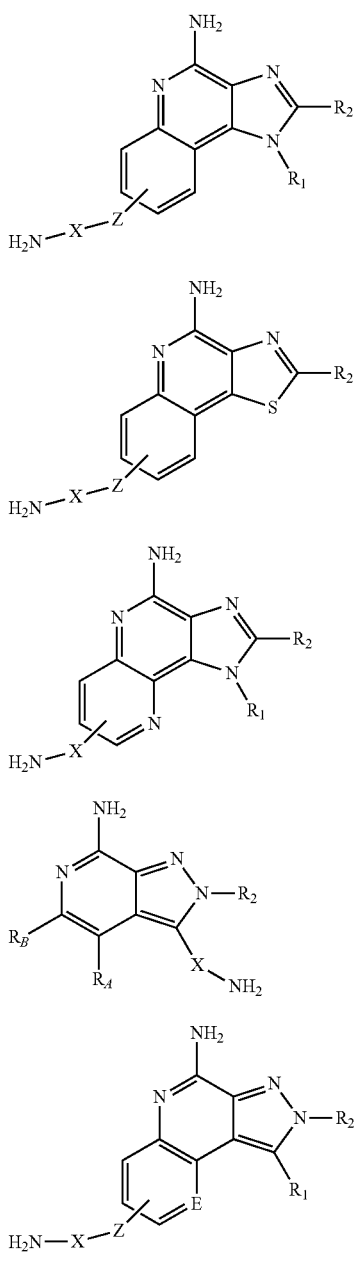

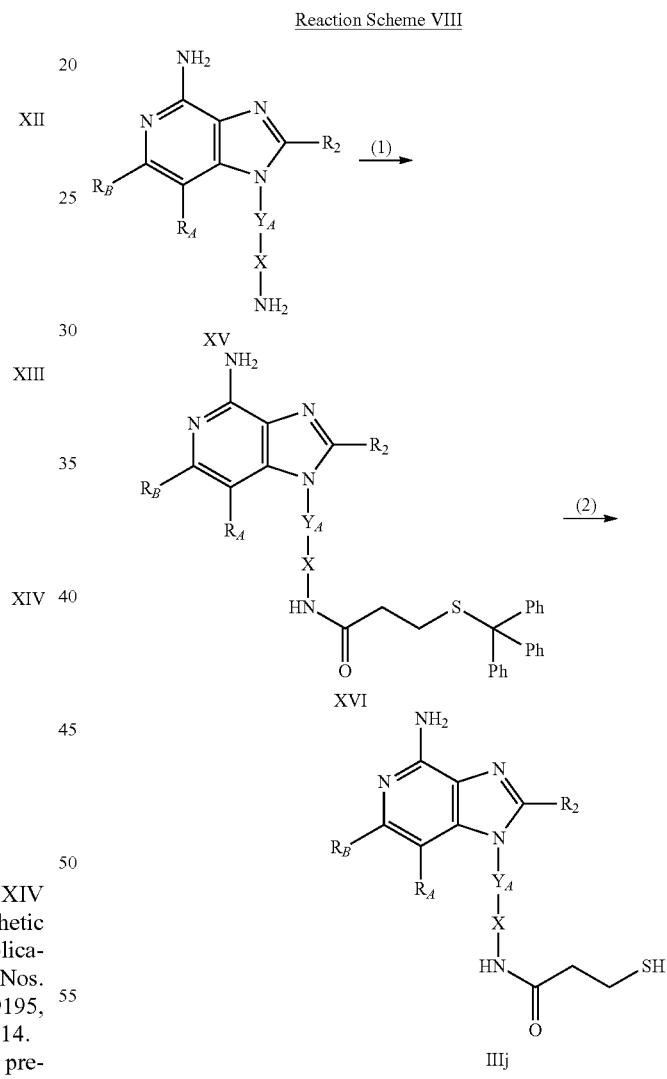

Many compounds of Formulas X, XI, XII, XIII, and XIV are known; others can be prepared using known synthetic methods. See for example, U.S. Patent Application Publication No. 2004/0147543; International Publication Nos. WO2005/020999, WO2005/032484, WO2005/079195, WO2006/009826, WO2006/038923 and WO2006/093514.

In some embodiments, functionalized IRMs can be prepared according to the method of Reaction Scheme VIII wherein $Y_A$ is defined as —NH— or —O—, and $R_2$, $R_A$, $R_B$, and X are as defined above. Many compounds of Formula XV are known; others can be prepared using known synthetic methods. See for example, U.S. Pat. No. 7,163,947 and International Publication Nos. WO2006/026760 and WO2006/028962.

In step (1) of Reaction Scheme VIII, a compound of Formula XV or a salt thereof is acylated with succinimido 3-(triphenylmethylthio)propanoate (A. Bray et. al. *Aust. J. Chem.* 1990, 43, 629-634). The reaction is carried out in a suitable solvent such as dichloromethane or methanol or a mixture thereof. A base such as triethylamine can be added if a salt of a compound of Formula XV is used as the starting material. The reaction can be carried out at ambient temperature.

In step (2) of Reaction Scheme VIII, the triphenylmethyl protecting group on a compound of Formula XVI is removed to provide a functionalized IRM of Formula IIIj. The reaction is carried out using an acid such as trifluoroacetic acid and a silane such as triethylsilane in a suitable solvent such as dichloromethane. The product of Formula IIIj, or a pharmaceutically acceptable salt thereof, can be isolated using conventional methods.

In some embodiments, functionalized IRMs can be prepared according to the method of Reaction Scheme IX wherein $R_1$ and $R_2$ are as defined above. Many compounds of Formula XVII are known; others can be prepared using known synthetic methods. See for example, International Publication No. WO2005/032484.

In step (1) of Reaction Scheme IX, a compound of Formula XVII or a salt thereof is converted to an ether-substituted compound of Formula XVIII using a Williamson-type ether synthesis. A compound of Formula XVII is alkylated with a linker containing a protected $FG_A$, for example, a linker such as 13-oxo-17,17,17-triphenyl-3,6,9-trioxa-16-thia-12-aza-heptadec-1-yl methanesulfonate, prepared as described below. The reaction is conveniently carried out by combining the methanesulfonate with a compound of Formula XVII in a solvent such as DMF in the presence of a suitable base such as cesium carbonate. The reaction can be carried out at ambient temperature or at an elevated temperature, for example, 65° C. or 85° C.

In step (2) of Reaction Scheme IX, a compound of Formula XVIII is deprotected using the reaction conditions described in step (2) of Reaction Scheme VIII to provide a functionalized IRM of Formula IIIk. The product of Formula IIIk, or a pharmaceutically acceptable salt thereof, can be isolated using conventional methods.

Also shown in Reaction Scheme IX, a compound of Formula XVII can be elaborated into a compound of Formula XIX using the methods described in International Publication No. WO2005/032484. A compound of Formula XIX can be elaborated as described in Reaction Scheme VIII to provide functionalized IRM of Formula IIIm. The product of Formula IIIM, or a pharmaceutically acceptable salt thereof, can be isolated using conventional methods.

In Reaction Scheme X, a compound of Formula XX or a salt thereof is converted into a functionalized IRM of Formula IIIn using the methods described in Reaction Scheme VIII.

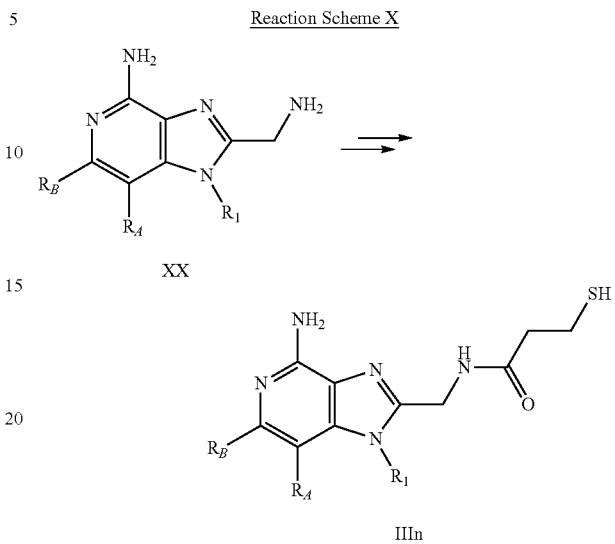

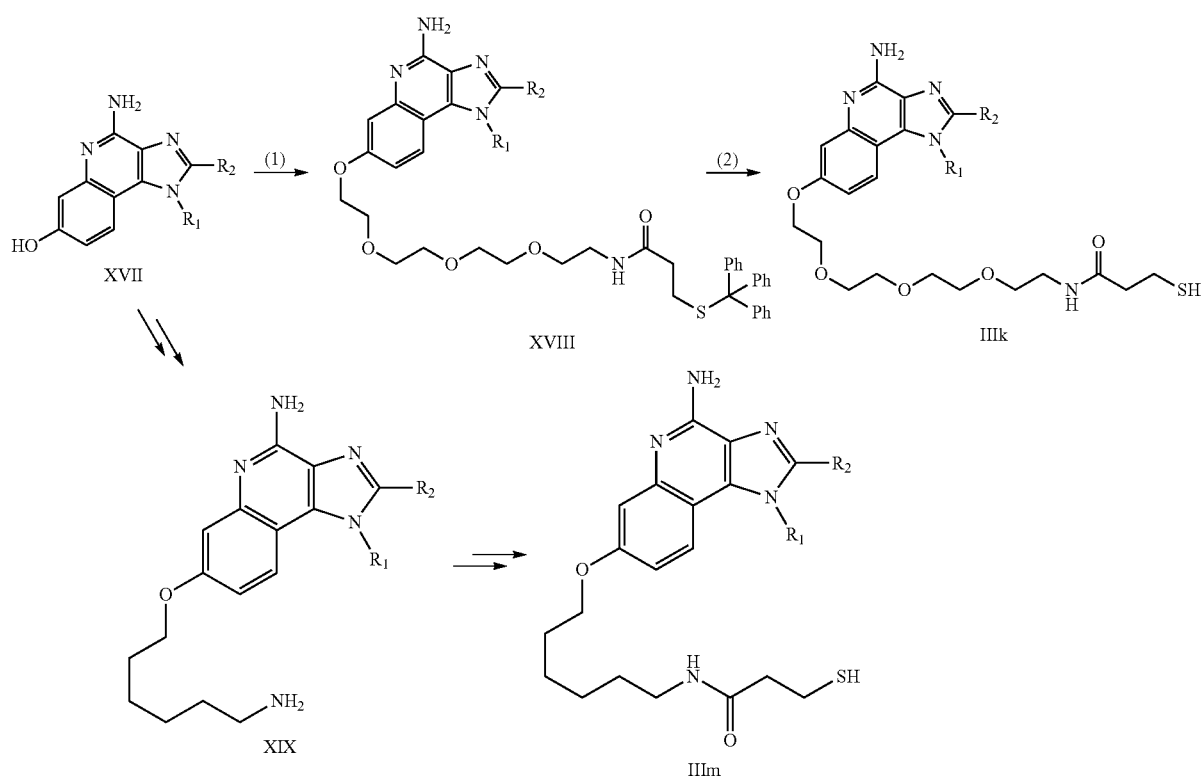

In some embodiments, functionalized IRMs can be prepared according to the method of Reaction Scheme X wherein $R_1$, $R_A$, $R_B$, are as defined above. Compounds of Formula XX are known; see, for example, International Publication No. WO2005/123079.

In some embodiments, functionalized IRMs can be prepared according to the method of Reaction Scheme XI wherein $R_2$, $R_A$, $R_B$, are as defined above. Compounds of Formula XXI are known; see, for example, U.S. Patent Application Publication No. US 2006/0100229.

In Reaction Scheme XI, a compound of Formula XXI is reacted with 4-maleimidobutyric acid to provide a functionalized IRM of Formula IIIo. The coupling reaction can be carried out as described in step (1) of Reaction Scheme V. The product of Formula IIIo, or a pharmaceutically acceptable salt thereof, can be isolated using conventional methods.

Reaction Scheme XI

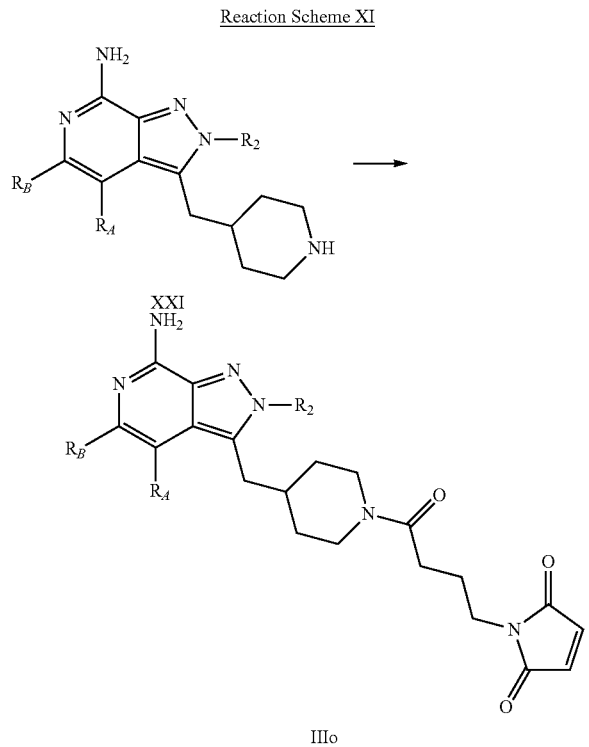

In some embodiments, the functional group $FG_A$ on the IRM of Formula III, which is intended to react with an appropriate functional group $FG_B$ on the SAM of Formula I, may not be compatible with certain functional groups in the IRM. For example, a compound of Formula IV contains an amine at the 4-position of the 1H-imidazo[4,5-c]pyridine core. Also, compounds of Formulas IV, X, XI, and XII may contain a hydroxyl group on the $R_1$ or $R_2$ group. The amino or hydroxyl group may react with certain electrophilic functional groups $FG_A$ including, but not limited to, activated carboxylic acids and activated carbonates such as those listed above, isocyanates, and thioisocyanates. The same amino or hydroxyl group may also interfere in a similar manner with the synthesis of a compound of Formula III. In these cases, it may be necessary to use a protecting group or prodrug group, to temporarily mask the reactivity of the amino or hydroxyl group. The protecting group may then be removed at the appropriate step in the synthetic route. For example, as illustrated in Reaction Scheme VII, a compound of Formula IV can be reacted with succinic anhydride to protect the 4-amine as the corresponding succinimide. The protected compound may be elaborated using conventional methods to include an electrophilic functional group $FG_A$, such as those described above, that may react with an amine. The succinimide protecting group may be removed by cleavage with hydrazine. In another example, the amino group on an IRM may be protected temporarily with a suitable protecting group while an isocyanate or chloroformate is formed elsewhere in the IRM, such as, for example in the $R_1$ or $R_2$ group, and is reacted with an amino or alcohol group on a linker group to form a carbamate or carbonate linkage. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

In some embodiments of the invention, a prodrug of the IRM can be used. The term "prodrug" means a compound that can be transformed in vivo to yield an immune response modifying compound. The prodrug, itself, may be an immune response modifying compound. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

A prodrug can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, C$_{1-6}$ alkyl, and benzyl; Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-14}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl. Particularly useful prodrugs are amides derived from carboxylic acids containing one to ten carbon atoms, amides derived from amino acids, and carbamates containing one to ten carbon atoms.

Alternatively, prodrugs can be prepared by the replacement of the hydrogen atom of hydroxy group using conventional methods with a group such as X$_2$—C(O)—R', α-aminoacyl, α-aminoacyl-α-aminoacyl, —X$_2$—C(O)—O—R', and —C(O)—N(R")R'; wherein X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—; R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and each α-aminoacyl is an α-aminoacyl group derived from an α-amino acid selected from the group consisting of racemic, D-, and L-amino acids. Particularly useful prodrugs are esters made from carboxylic acids containing one to six carbon atoms, unsubstituted or substituted benzoic acid esters, or esters made from naturally occurring amino acids.

Unless otherwise specified, as used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl(azepanyl), 1,4-oxazepanyl, homopiperazinyl(diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected. In another example, when two $R_{10}$ groups are present each $R_{10}$ group is independently selected.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

In the examples below normal high performance flash chromatography (HPFC) was carried out using a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Preparation of the Functionalized IRM Compounds of Formula III

IRM Compound 1 (IRM1)

N-{2-[4-Amino-2-(ethoxymethyl)-1H-imidazo[4,5-c]quinolin-1-yl]-1,1-dimethylethyl}-6-[(3-mercaptopropanoyl)amino]hexanamide

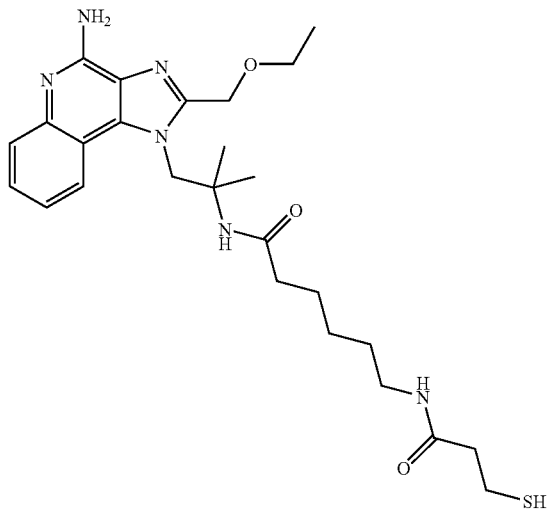 [SMILES: CCOCc1nc2c(N)nc3ccccc3c2n1CC(C)(C)NC(=O)CCCCCNC(=O)CCS]

Part A

To a solution of 6-(carbobenzyloxyamino) caproic acid (8.49 grams (g), 32.0 millimole (mmol)) in DMF (50 mL) at 0° C. was added N-hydroxysuccinimide and 1-(3-dimethylaminopropyl)-3-ethylcarbodiimide hydrochloride (EDC). After a short period, the solution was added to a 0° C. solution of 1-(2-amino-2-methylpropyl)-2-(ethoxymethyl)-1H-imidazo[4,5-c]quinolin-4-amine (prepared as described in U.S. Patent Publication No. 2004/0091491, 10 g, 32 mmol) in DMF (100 mL). The mixture was allowed to warm to room temperature and was stirred for 3 days. The solution was diluted with water (400 mL) and extracted with ethyl acetate (3×). The organic layers were combined and washed with water (2×) and brine. The organic layer was dried over sodium sulfate, filtered, and concentrated. The crude product was purified by HPFC on silica gel three times (gradient elution with CMA in chloroform) to provide 4.90 g of benzyl 6-({2-[4-amino-2-(ethoxymethyl)-1H-imidazo[4,5-c]quinolin-1-yl]-1,1-dimethylethyl}amino)-6-oxohexylcarbamate as a white foam.

Part B

A mixture of benzyl 6-({2-[4-amino-2-(ethoxymethyl)-1H-imidazo[4,5-c]quinolin-1-yl]-1,1-dimethylethyl}amino)-6-oxohexylcarbamate (4.90 g, 8.75 mmol) and 10% palladium on carbon (0.5 g) in ethanol (100 mL) was hydrogenated on a Parr apparatus at 20-40 psi (1.4× $10^5$-2.8×$10^5$ Pa) for 1 day, during which time fresh hydrogen was introduced several times. The mixture was filtered through CELITE filter agent. The filtrate was concentrated under reduced pressure to yield a white foam that was used directly in the next step.

Part C

To a mixture of 3,3'-dithiodipropionic acid (920 mg, 4.38 mmol) and 1-hydroxybenzotriazole (HOBT) (1.42 g, 10.5 mmol) in dimethylformamide (DMF) (50 mL) at 0° C. was added 1-(3-dimethylaminopropyl)-3-ethylcarbodiimide hydrochloride (1.85 g, 9.63 mmol). The mixture was stirred at 0° C. for 4 hours. The material from Part B (8.75 mmol) was dissolved in DMF (20 mL), cooled to 0° C., and the cold solution of the activated diacid was added in one portion, with two DMF rinses (10 mL each). The reaction was allowed to warm slowly to room temperature overnight. Several more portions of EDC were added to the reaction at 0° C. over the next two days. The reaction was allowed to stir at room temperature for several days more, then was diluted with water and saturated aqueous sodium bicarbonate and was extracted with ethyl acetate several times. The combined organic extracts were washed with water and brine, and were concentrated under reduced pressure. The crude product was purified by HPFC to give 3.8 g of the disulfide dimer of N-{2-[4-amino-2-(ethoxymethyl)-1H-imidazo[4,5-c]quinolin-1-yl]-1,1-dimethylethyl}-6-[(3-mercaptopropanoyl)amino]hexanamide.

Part D

The material from Part C (3.8 g, 3.7 mmol) was dissolved in methanol (30 mL) at room temperature. Tris(2-carboxyethyl)phosphine hydrochloride (1.38 g, 4.81 mmol) was added, followed by water (3 mL), and 12.5 M aqueous sodium hydroxide (1.12 mL, 14.1 mmol). The solution was stirred at room temperature for 2 hours and then was cooled to 0° C. The solution was adjusted to pH 6 with 1 M aqueous hydrochloric acid (approximately 14 mL). The methanol was removed under reduced pressure and aqueous sodium bicarbonate was added. The mixture was extracted with dichloromethane (3×). The organic extracts were combined, washed with water and brine, dried over sodium sulfate, filtered, and concentrated. The crude product was purified by HPFC on silica gel (gradient elution with 0-50% CMA in chloroform). The appropriate fractions were concentrated to provide 2.36 g of N-{2-[4-amino-2-(ethoxymethyl)-1H-imidazo[4,5-c]quinolin-1-yl]-1,1-dimethylethyl}-6-[(3-mercaptopropanoyl)amino]hexanamide.

White foam, MS (ESI) m/z 515 (M+H)$^+$. $^1$H NMR (300 MHz, CDCl$_3$) δ 8.22 (dd, 1H), 7.80 (dd, 1H), 7.51 (ddd, 1H), 7.32 (ddd, 1H), 5.96 (m, 1H), 5.59 (s, 1H), 5.51 (br s, 2H), 5.06 (s, 2H), 4.84 (br s, 2H), 3.62 (q, J=6.9 Hz, 2H), 3.25 (q, J=6.9 Hz, 2H), 2.81 (m, 2H), 2.50 (t, J=6.9 Hz, 2H), 1.98 (m, 2H), 1.61-1.18 (m, 13H), 1.24 (t, J=6.9 Hz, 3H). Anal. calcd for $C_{26}H_{38}N_6O_3S \cdot 0.5H_2O$: C, 59.63; H, 7.51; N, 16.05; S, 6.12. Found: C, 59.89; H, 7.66; N, 16.22; S, 6.25.

IRM Compound 2 (IRM2)

N-{2-[4-Amino-2-(ethoxymethyl)-1H-imidazo[4,5-c]quinolin-1-yl]-1,1-dimethylethyl}-6-{[3-(pyridin-2-yldithio)propanoyl]amino}hexanamide

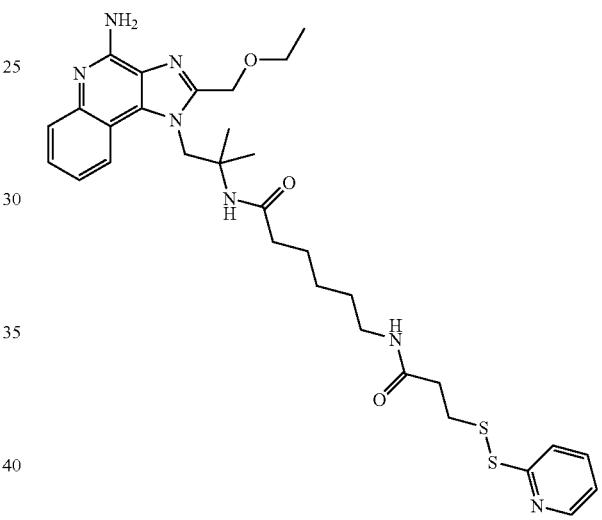

A solution of N-{2-[4-amino-2-(ethoxymethyl)-1H-imidazo[4,5-c]quinolin-1-yl]-1,1-dimethylethyl}-6-[(3-mercaptopropanoyl)amino]hexanamide (1.33 g, 2.58 mmol) in dichloromethane (16 mL) was added dropwise over 1.5 hours to a solution of 2,2'-dipyridyl disulfide (2.27 g, 10.3 mmol) in dichloromethane (10 mL). The solution was stirred at room temperature for 18 hours, then was concentrated under reduced pressure. The residue was purified by HPFC on silica gel twice (gradient elution with 1-10% methanol in dichloromethane) to yield 800 mg of N-{2-[4-amino-2-(ethoxymethyl)-1H-imidazo[4,5-c]quinolin-1-yl]-1,1-dimethylethyl}-6-{[3-(pyridin-2-yldithio)propanoyl]amino}hexanamide as a white foam.

Alternatively, N-{2-[4-amino-2-(ethoxymethyl)-1H-imidazo[4,5-c]quinolin-1-yl]-1,1-dimethylethyl}-6-{[3-(pyridin-2-yldithio)propanoyl]amino}hexanamide was synthesized from 6-amino-N-{2-[4-amino-2-(ethoxymethyl)-1H-imidazo[4,5-c]quinolin-1-yl]-1,1-dimethylethyl}hexanamide hydrochloride in one step. A mixture of 6-amino-N-{2-[4-amino-2-(ethoxymethyl)-1H-imidazo[4,5-c]quinolin-1-yl]-1,1-dimethylethyl}hexanamide hydrochloride (68 mg, 0.16 mmol), triethylamine (0.046 mL, 0.32 mmol), and N-succinimidyl 3-(2-pyridyldithio)propionate in tetrahydrofuran (1.6 mL) and DMF (0.5 mL) was stirred at room temperature for 5 hours. The reaction mixture was partitioned between water and ethyl acetate. The aqueous phase was extracted with ethyl acetate. The organic layers were combined, washed with water and brine, dried over sodium sulfate, filtered, and concentrated under reduced pressure. The crude product was purified by chromatography on silica gel to provide 36 mg of N-{2-[4-amino-2-(ethoxymethyl)-1H-imidazo[4,5-c]quinolin-1-yl]-1,1-dimethylethyl}-6-{[3-pyridin-2-yldithio)propanoyl]amino}hexanamide as a colorless oil.

MS (ESI) m/z 624 (M+H)+. 1H NMR (300 MHz, CDCl3) δ 8.43 (m, 1H), 8.23 (m, 1H), 7.80 (m, 1H), 7.63 (m, 2H), 7.50 (m, 1H), 7.32 (m, 1H), 7.11 sextet, J=4.4 Hz, 1H), 6.52 (m, 1H), 5.55 (s, 1H), 5.47 (br s, 2H), 5.07 (s, 2H), 4.83 (br s, 2H), 3.62 (q, J=6.9 Hz, 2H), 3.27 (q, 2H), 3.08 (t, J=6.9 Hz, 2H), 2.61 (t, 2H), 2.04-1.99 (m, 2H), 1.67-1.22 (m, 12H), 1.24 (t, J=7.0 Hz, 3H). Anal. calcd for $C_{31}H_{41}N_7O_3S_2 \cdot 1.0H_2O$: C, 58.01; H, 6.75; N, 15.28; S, 9.99. Found: C, 58.37; H, 6.69; N, 15.24; S, 9.99.

IRM Compound 3 (IRM3)

N-[4-(4-Amino-2-butyl-1H-imidazo[4,5-c]quinolin-1-yl)butyl]-3-mercaptopropanamide

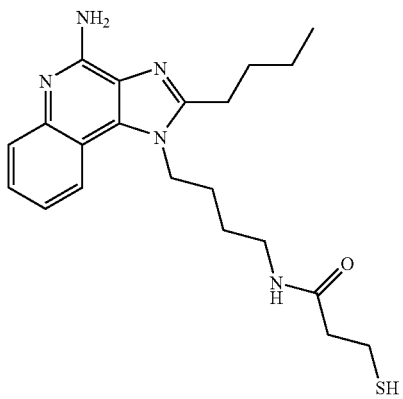 [SMILES: CCCCc1nc2c(N)nc3ccccc3c2n1CCCCNC(=O)CCS]

Part A

Following a procedure similar to that described above in Part C of IRM Compound 1, 1,1-(4-aminobutyl)-2-butyl-1H-imidazo[4,5-c]quinolin-4-amine (U.S. Pat. No. 6,451,810 and references cited therein, 1.00 g, 3.21 mmol) was converted into 1.05 g of the disulfide dimer of N-[4-(4-amino-2-butyl-1H-imidazo[4,5-c]quinolin-1-yl)butyl]-3-mercaptopropanamide.

Part B

Following a procedure similar to that described above in Part D of IRM Compound 1, the disulfide dimer of N-[4-(4-amino-2-butyl-1H-imidazo[4,5-c]quinolin-1-yl)butyl]-3-mercaptopropanamide (0.78 g, 0.98 mmol) was converted into 600 mg of N-[4-(4-amino-2-butyl-1H-imidazo[4,5-c]quinolin-1-yl)butyl]-3-mercaptopropanamide after purification by HPFC on silica gel (gradient elution with 2-30% CMA in chloroform)

White solid, mp 133.0-135.0° C. MS (ESI) m/z 400 (M+H)+. 1H NMR (300 MHz, CDCl3) δ 7.90 (dd, J=8.1, 1.2 Hz, 1H), 7.82 (dd, J=8.1, 1.2 Hz, 1H), 7.50 (m, 1H), 7.32 (m, 1H), 5.50 (m, 1H), 5.34 (br s, 2H), 4.49 (t, J=7.5 Hz, 2H), 3.34 (q, J=6.8 Hz, 2H), 2.90 (m, 2H), 2.77 (q, J=6.9 Hz, 2H), 2.41 (t, J=6.8 Hz, 2H), 2.03-1.82 (m, 4H), 1.73-1.45 (m, 5H), 1.01 (t, J=7.5 Hz, 3H). Anal. calcd for $C_{21}H_{29}N_5OS$: C, 63.13; H, 7.32; N, 17.53. Found: C, 63.14; H, 7.36; N, 17.84.

IRM Compound 4 (IRM4)

N-[4-(4-Amino-2-butyl-1H-imidazo[4,5-c]quinolin-1-yl)butyl]-3-(pyridin-2-yldithio)propanamide

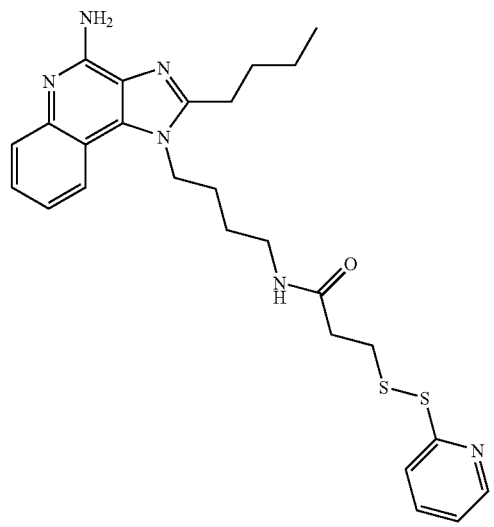 [SMILES: CCCCc1nc2c(N)nc3ccccc3c2n1CCCCNC(=O)CCSSc1ccccn1]

Part A

Following a procedure similar to that described above in Part A of IRM Compound 2, N-[4-(4-amino-2-butyl-1H-imidazo[4,5-c]quinolin-1-yl)butyl]-3-mercaptopropanamide (0.20 g, 0.50 mmol) was converted into 47 mg of N-[4-(4-amino-2-butyl-1H-imidazo[4,5-c]quinolin-1-yl)butyl]-3-(pyridin-2-yldithio)propanamide.

Yellow glassy solid, mp 63.0-73.0° C. MS (ESI) m/z 509 (M+H)+. 1H NMR (300 MHz, CDCl3) δ 8.33 (m, 1H), 7.89 (m, 1H), 7.81 (m, 1H), 7.61-7.46 (m, 3H), 7.30 (m, 1H), 7.05 (m, 1H), 6.77 (m, 1H), 5.49 (br s, 2H), 4.47 (t, J=7.5 Hz, 2H), 3.37 (q, J=6.5 Hz, 2H), 3.04 (m, 2H), 2.88 (m, 2H), 2.55 (t, J=6.5 Hz, 2H), 2.05-1.66 (m, 6H), 1.49 (sextet, J=7.5 Hz, 2H), 0.99 (t, J=7.5 Hz, 3H). Anal. calcd for $C_{26}H_{32}N_6OS_2 \cdot 0.6H_2O$: C, 60.11; H, 6.44; N, 16.18. Found: C, 59.80; H, 6.23; N, 16.25.

IRM Compound 5 (IRM5)

N-{2-[4-Amino-2-(ethoxymethyl)-1H-imidazo[4,5-c]quinolin-1-yl]-1,1-dimethylethyl}-4-hydrazino-4-oxobutanamide

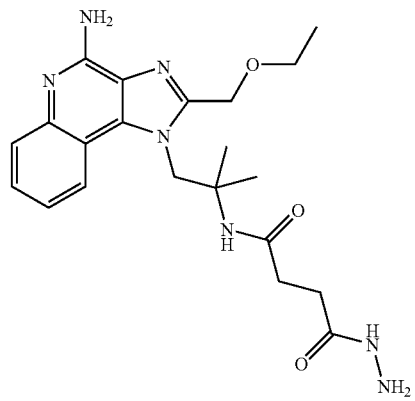 [SMILES: CCOCc1nc2c(N)nc3ccccc3c2n1CC(C)(C)NC(=O)CCC(=O)NN]

Part A

Succinic anhydride (3.20 g, 32.0 mmol) was added to a 100° C. solution of 1-(2-amino-2-methylpropyl)-2-(ethoxymethyl)-1H-imidazo[4,5-c]quinolin-4-amine (prepared as described in U.S. Patent Publication No. 2004/0091491, 2.00 g, 6.39 mmol) in DMF (20 mL). After 2 days, the reaction mixture was concentrated under reduced pressure to give an off-white solid. The solid was stirred with 100 mL of dichloromethane and was isolated by filtration. The filtrate was concentrated, stirred with dichloromethane (25 mL), and filtered to yield additional solid. The combined solids were dried under vacuum to give 3.16 g of 4-({2-[4-(2,5-dioxopyrrolidin-1-yl)-2-(ethoxymethyl)-1H-imidazo[4,5-c]quinolin-1-yl]-1,1-dimethylethyl}amino)-4-oxobutanoic acid as a white solid that was used without further purification.

Part B

A solution of 4-({2-[4-(2,5-dioxopyrrolidin-1-yl)-2-(ethoxymethyl)-1H-imidazo[4,5-c]quinolin-1-yl]-1,1-dimethylethyl}amino)-4-oxobutanoic acid (3.16 g, 6.39 mmol) in dichloromethane (100 mL) was treated with triethylamine (2.67 mL, 19.2 mmol), 1-(3-dimethylaminopropyl)-3-ethylcarbodiimide hydrochloride (3.67 g, 19.2 mmol), tert-butylcarbazate (2.46 g, 19.2 mmol) and N,N-dimethylpyridin-4-amine (78 mg, 0.64 mmol). The reaction mixture was stirred for 4 days and then was treated with 100 mL of water. The layers were separated and the aqueous portion was extracted with chloroform (50 mL). The combined organic layers were washed successively with water (50 mL) and brine (50 mL). The organic portion was dried over sodium sulfate, filtered, and concentrated under reduced pressure to give a white foam. The white foam was dissolved in dichloromethane (50 mL) and treated with ethylene diamine (1 mL). After stirring for 4 hours, the reaction mixture was treated with water (50 mL) and chloroform (50 mL) and the layers were separated. The aqueous portion was extracted with chloroform (2×25 mL). The combined organic layers were washed with water (50 mL) and brine (50 mL). The organic layer was concentrated and purification of the crude product by chromatography on silica gel (gradient elution, 25%-100% CMA in chloroform) followed by crystallization from dichloromethane gave 1.67 g of tert-butyl 2-[4-({2-[4-amino-2-(ethoxymethyl)-1H-imidazo[4,5-c]quinolin-1-yl]-1,1-dimethylethyl}amino)-4-oxobutanoyl]hydrazinecarboxylate as a white powder.

Part C

A solution of tert-butyl 2-[4-({2-[4-amino-2-(ethoxymethyl)-1H-imidazo[4,5-c]quinolin-1-yl]-1,1-dimethylethyl}amino)-4-oxobutanoyl]hydrazinecarboxylate (792 mg, 1.50 mmol) in dichloromethane (30 mL) was treated with trifluoroacetic acid (3 mL). After stirring for 2 hours, additional trifluoroacetic acid (3 mL) was added to the reaction mixture and stirring was continued for 1 hour. The reaction mixture was concentrated under reduced pressure and the resulting syrup was dissolved in water. The solution was made basic by the addition of concentrated ammonium hydroxide and then was extracted repeatedly with 10% methanol/chloroform. The combined organic portions were dried over sodium sulfate, filtered, and concentrated under reduced pressure. The crude white solid was purified by chromatography on silica gel (gradient elution, 25%-75% CMA in chloroform) gave 340 mg of N-{2-[4-amino-2-(ethoxymethyl)-1H-imidazo[4,5-c]quinolin-1-yl]-1,1-dimethylethyl}-4-hydrazino-4-oxobutanamide.

White solid, mp 203.0-204.6° C. $^1$H NMR (300 MHz, DMSO-$d_6$) δ 8.98 (s, 1H), 8.32 (d, J=7.4 Hz, 1H), 7.74 (s, 1H), 7.60 (dd, J=8.3, 1.2, Hz, 1H), 7.41 (m, 1H), 7.23 (ddd, J=8.2, 7.0, 1.2 Hz, 1H), 6.59 (s, 2H), 4.99 (br s, 2H), 4.72 (br s, 2H), 4.16 (br s, 2H), 3.51 (q, J=7.0 Hz, 2H), 2.34-2.24 (m, 4H), 1.20 (br s, 6H), 1.13 (t, J=7.0 Hz, 3H); $^{13}$C NMR (125 MHz, DMSO-$d_6$) δ 172.3, 171.2, 152.4, 150.7, 145.8, 134.5, 127.0, 126.8, 126.7, 121.5, 121.0, 115.6, 65.8, 64.6, 55.1, 51.4, 31.8, 29.1, 25.9, 15.3; MS (ESI) m/z 428 (M+H)$^+$; Anal. Calcd for $C_{21}H_{29}N_7O_3 \cdot 0.5H_2O$: C, 57.78; H, 6.93; N, 22.46. Found: C, 58.00; H, 6.69; N, 22.36.

IRM Compound 6 (IRM6)

N-{2-[4-Amino-2-(ethoxymethyl)-1H-imidazo[4,5-c]quinolin-1-yl]-1,1-dimethylethyl}-6-{[3-(2,5-dioxo-2,5-dihydro-1H-pyrrol-1-yl)propanoyl]amino}hexanamide

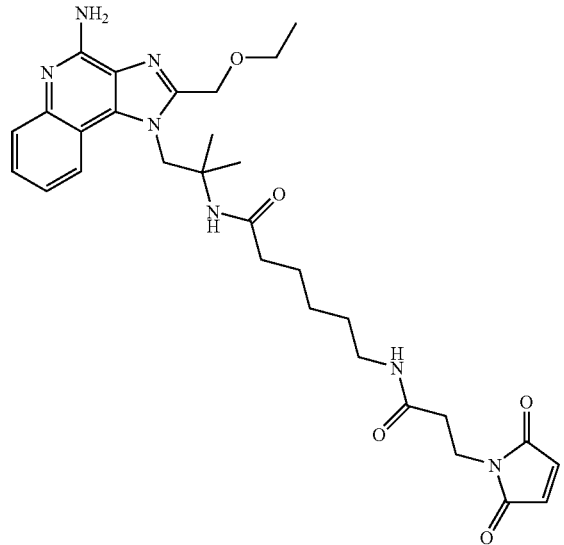 [SMILES: CCOCc1nc2c(N)nc3ccccc3c2n1CC(C)(C)NC(=O)CCCCCNC(=O)CCN1C(=O)C=CC1=O]

Part A

To a solution of 6-amino-N-{2-[4-amino-2-(ethoxymethyl)-1H-imidazo[4,5-c]quinolin-1-yl]-1,1-dimethylethyl}hexanamide (28 mg, 0.66 mmol, prepared as generally described in Part A-B of IRM Compound 1) in dichloromethane (0.5 mL) at room temperature was added N-succinimidyl-3-maleimidopropionate (18 mg, 0.68 mmol). The mixture was shaken until the reagent dissolved, allowed to stand for 30 minutes, then concentrated under reduced pressure. The foam was purified by reverse phase HPLC using 0.05% formic acid/acetonitrile in 0.05% formic acid/water as the eluent to yield 11 mg of N-{2-[4-amino-2-(ethoxymethyl)-1H-imidazo[4,5-c]quinolin-1-yl]-1,1-dimethylethyl}-6-{[3-(2,5-dioxo-2,5-dihydro-1H-pyrrol-1-yl)propanoyl]amino}hexanamide as the monoformate salt.

Off white glassy solid, MS (ESI) m/z 578 (M+H)$^+$. $^1$H NMR (300 MHz, DMSO-$d_6$) δ 8.34 (d, J=7.5 Hz, 1H), 8.22 (s, 2H), 7.90 (t, J=5.3 Hz, 1H), 7.65 (s, 1H), 7.60 (dd, J=8.4, 1.2 Hz, 1H), 7.42 (m, 1H), 7.22 (m, 1H), 7.00 (s, 2H), 6.67 (br s, 2H), 5.00 (br s, 2H), 4.74 (br, 2H), 3.59 (t, J=7.3 Hz, 2H), 3.51 (q, J=7.0 Hz, 2H), 2.98 (q, J=6.3 Hz, 2H), 2.31 (t, J=7.2 Hz, 2H), 2.04 (t, J=7.4 Hz, 2H), 1.47 (m, 2H), 1.36 (m, 2H), 1.20 (m, 8H), 1.13 (t, J=7.0 Hz, 3H).

IRM Compound 7 (IRM7)

1-(4-{4-[(4-Amino-2-propyl-2H-pyrazolo[3,4-c]quinolin-1-yl)methyl]piperidin-1-yl}-4-oxobutyl)-1H-pyrrole-2,5-dione

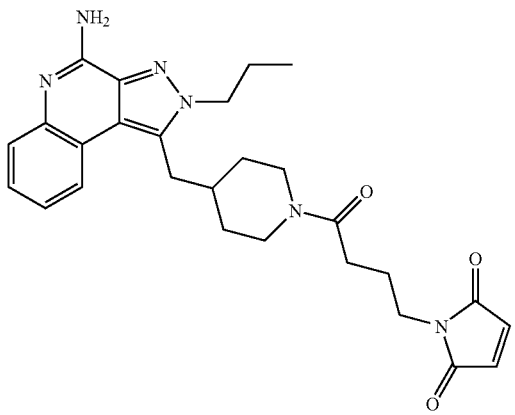 [SMILES: CCCn1nc2c(N)nc3ccccc3c2c1CC1CCN(C(=O)CCCN2C(=O)C=CC2=O)CC1]

1-(3-Dimethylaminopropyl)-3-ethylcarbodiimide hydrochloride (0.266 g, 1.39 mmol) was added to a mixture of 4-maleimidobutyric acid (0.254 g, 1.39 mmol) and 1-hydroxybenzotriazole (0.187 g, 1.39 mmol) in DMF (13 mL). The mixture was stirred for 1 hour, then 1-(piperidin-4-ylmethyl)-2-propyl-2H-pyrazolo[3,4-c]quinolin-4-amine (0.450 g, 1.39 mmol) was added. The mixture was stirred for 1 hour, then water (60 mL) was added, and the mixture was stirred an additional hour. The aqueous layer was extracted with ethyl acetate (2×75 mL) and dichloromethane (2×75 mL). The organic layers were combined, washed with water (2×100 mL) and brine, and then concentrated under reduced pressure. The resulting residue was purified by HPFC on silica gel (gradient elution with 2-20% CMA in chloroform) to provide 0.251 g of 1-(4-{4-[(4-amino-2-propyl-2H-pyrazolo[3,4-c]quinolin-1-yl)methyl]piperidin-1-yl}-4-oxobutyl)-1H-pyrrole-2,5-dione as a yellow foam. Anal. Calcd for $C_{27}H_{32}N_6O_3 \cdot 0.75H_2O$: C, 64.36; H, 6.68; N, 16.53. Found: C, 64.59; H, 6.73; N, 16.74.

IRM Compound 8 (IRM8)

N-{3-[(4-Amino-2-methyl-1H-imidazo[4,5-c]quinolin-1-yl)amino]propyl}-3-mercaptopropanamide

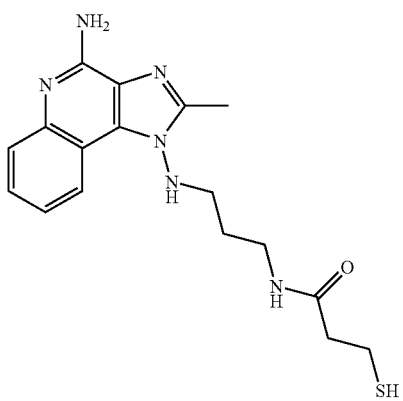 [SMILES: Cc1nc2c(N)nc3ccccc3c2n1NCCCNC(=O)CCS]

A mixture of $N^1$-(3-aminopropyl)-2-methyl-1H-imidazo[4,5-c]quinoline-1,4-diamine hydrochloride (1.00 g, 3.26 mmol), succinimido 3-(triphenylmethylthio)propanoate (A. Bray et. al. Aust. J. Chem. 1990, 43, 629-634; 2.22 g, 4.89 mmol), triethylamine (0.45 mL, 3.26 mmol), dichloromethane (33 mL), and methanol (15 mL) was stirred overnight at room temperature. The reaction mixture was concentrated under reduced pressure and the residue was purified by flash chromatography on silica gel (gradient elution with a solution of 2% ammonium hydroxide in methanol and chloroform). The purified compound was treated with trifluoroacetic acid (3 mL) and triethylsilane (2 mL) in dichloromethane (30 mL) at room temperature overnight. More trifluoroacetic acid was added and after an additional day the reaction was complete. The reaction mixture was concentrated under reduced pressure and purified by flash chromatography on silica gel (gradient elution with a solution of 2% ammonium hydroxide in methanol and chloroform) to yield 327 mg of N-{3-[(4-amino-2-methyl-1H-imidazo[4,5-c]quinolin-1-yl)amino]propyl}-3-mercaptopropanamide. MS (ESI) m/z 359 (M+H)$^+$.

IRM Compound 9 (IRM9)

N-(2-{2-[2-(2-{[4-Amino-2-(ethoxymethyl)-1-(2-hydroxy-2-methylpropyl)-1H-imidazo[4,5-c]quinolin-7-yl]oxy}ethoxy)ethoxy]ethoxy}ethyl)-3-mercaptopropanamide

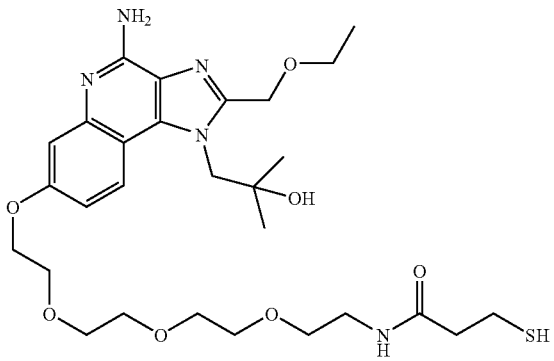 [SMILES: CCOCc1nc2c(N)nc3cc(OCCOCCOCCOCCNC(=O)CCS)ccc3c2n1CC(C)(C)O]

Part A

Succinimido 3-(triphenylmethylthio)propanoate (4.06 mg, 9.12 mmol) was added to a 0° C. solution of 2-{2-[2-(2-aminoethoxy)ethoxy]ethoxy}ethanol (C. Bertozzi and M. Bednarski, J. Org. Chem. 1991, 56, 4326-4329) (9.12 mmol) in dichloromethane (20 mL). The solution was stirred at room temperature for 2 days and concentrated ammonium hydroxide (1 mL) was added. After 20 minutes, the mixture was filtered and the filtrate was subjected to an extractive workup. The organic layer were dried over sodium sulfate and concentrated under reduced pressure. The crude product was purified by HPFC on silica gel (gradient elution with 2-19% CMA in chloroform) to provide 3.95 g of N-(2-{2-[2-(2-hydroxyethoxy)ethoxy]ethoxy}ethyl)-3-(tritylthio)propanamide as a colorless oil.

Part B

Methanesulfonyl chloride (0.55 mL, 7.1 mmol) was added to a 0° C. solution of N-(2-{2-[2-(2-hydroxyethoxy)ethoxy]ethoxy}ethyl)-3-(tritylthio)propanamide (3.38 g, 6.45 mmol) and triethylamine (1.08 mL, 7.74 mmol) in dichloromethane (33 mL). The solution was allowed to warm to room temperature. After 4 hours, the solution was diluted with dichloromethane and washed with water (2×) and brine. The organic phase was dried over sodium sulfate, filtered, and concentrated under reduced pressure to yield 4.71 g of 13-oxo-17,17,17-triphenyl-3,6,9-trioxa-16-thia-12-azaheptadec-1-yl methanesulfonate, which was concentrated from toluene and used in Part C.

Part C

A 1.61 M solution of the mesylate from Part B (1.29 mL, 3.46 mmol) in DMF was added to a 60° C. stirred mixture of 4-amino-2-(ethoxymethyl)-1-(2-hydroxy-2-methylpropyl)-1H-imidazo[4,5-c]quinolin-7-ol (1.12 g, 3.39 mmol) and cesium carbonate (2.21 g) in DMF (10 mL). Additional cesium carbonate (1.12 g) was added and heating was continued for 4 hours, during which time additional mesylate solution (0.7 mL) was added. The mixture was allowed to stand overnight at room temperature; then it was partitioned between ethyl acetate and water. The water layer was separated and extracted with ethyl acetate. The organic layer was washed with water and brine. The organic layer was dried over sodium sulfate, filtered, and concentrated under reduced pressure. The crude product was purified by HPFC on silica gel (gradient elution with 2-30% CMA in chloroform) to provide 1.38 g of N-(2-{2-[2-(2-{[4-amino-2-(ethoxymethyl)-1-(2-hydroxy-2-methylpropyl)-1H-imidazo[4,5-c]quinolin-7-yl]oxy}ethoxy)ethoxy]ethoxy}ethyl)-3-(tritylthio)propanamide as a white foam.

Part D

Trifluoroacetic acid (8 mL) was added to a 0° C. solution of N-(2-{2-[2-(2-{[4-amino-2-(ethoxymethyl)-1-(2-hydroxy-2-methylpropyl)-1H-imidazo[4,5-c]quinolin-7-yl]oxy}ethoxy)ethoxy]ethoxy}ethyl)-3-(tritylthio)propanamide (1.38 g, 1.65 mmol) and triethylsilane (3.16 mL, 19.8 mmol) in dichloromethane (12 mL). The solution was stirred at 0° C. for 2 hours, then was concentrated under reduced pressure. The residue was concentrated under reduced pressure from toluene several times. The crude product was purified twice by HPFC on silica gel (gradient elution with 2-70% CMA in chloroform) to provide 0.55 g of N-(2-{2-[2-(2-{[4-amino-2-(ethoxymethyl)-1-(2-hydroxy-2-methylpropyl)-1H-imidazo[4,5-c]quinolin-7-yl]oxy}ethoxy)ethoxy]ethoxy}ethyl)-3-mercaptopropanamide as a foam. MS (ESI) m/z 594 (M+H)+. Anal. Calcd for $C_{28}H_{43}N_5O_7S$: C, 56.64; H, 7.30; N, 11.80; S, 5.40. Found: C, 56.36; H, 7.52; N, 11.53; S, 5.34.

IRM Compound 10 (IRM10)

N-{6-[(4-Amino-2-(ethoxymethyl)-1-{2-methyl-2-[(methylsulfonyl)amino]propyl}-1H-imidazo[4,5-c]quinolin-7-yl)oxy]hexyl}-3-mercaptopropanamide

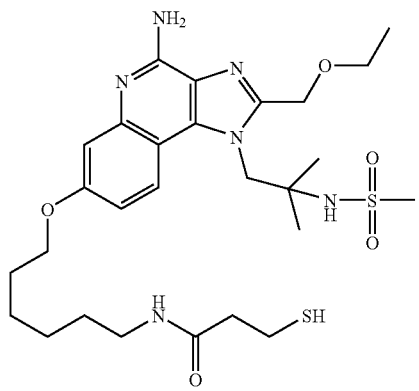 [SMILES: CCOCc1nc2c(N)nc3cc(OCCCCCCNC(=O)CCS)ccc3c2n1CC(C)(C)NS(C)(=O)=O]

Part A

Succinimido 3-(triphenylmethylthio)propanoate (246 mg, 0.553 mmol) was added to a 0° C. solution of N-{2-[4-amino-2-(ethoxymethyl)-7-hydroxy-1H-imidazo[4,5-c]quinolin-1-yl]-1,1-dimethylethyl}methanesulfonamide (280 mg, 0.553 mmol) in DMF (5 mL). The solution was stirred at 0° C. for 3 hours, then was diluted with ethyl acetate (100 mL) and washed with water (3×20 mL) and brine (40 mL). The organic phase was dried over sodium sulfate, filtered, and concentrated under reduced pressure. The crude product was purified by HPFC on silica gel (gradient elution with 2-50% CMA in chloroform) to provide 0.22 g of N-{6-[(4-amino-2-(ethoxymethyl)-1-{2-methyl-2-[(methylsulfonyl)amino]propyl}-1H-imidazo[4,5-c]quinolin-7-yl)oxy]hexyl}-3-(tritylthio)propanamide as a white solid.

Part B

Trifluoroacetic acid (1 mL) was added to a 0° C. solution of N-{6-[(4-amino-2-(ethoxymethyl)-1-{2-methyl-2-[(methylsulfonyl)amino]propyl}-1H-imidazo[4,5-c]quinolin-7-yl)oxy]hexyl}-3-(tritylthio)propanamide (0.22 g, 2.63 mmol) and triethylsilane (0.46 mL, 2.89 mmol) in dichloromethane (7 mL). The solution was stirred for 1 hour; then additional triethylsilane (0.05 mL) was added. After an additional hour at 0° C., the solution was concentrated under reduced pressure. The residue was concentrated under reduced pressure from ethyl acetate and toluene. The material was purified by HPFC on silica gel (gradient elution with 25-100% CMA in chloroform) and then subjected to the procedure described in Part D of the synthesis of IRM Compound 1 to provide 51 mg of N-{6-[(4-amino-2-(ethoxymethyl)-1-{2-methyl-2-[(methylsulfonyl)amino]propyl}-1H-imidazo[4,5-c]quinolin-7-yl)oxy]hexyl}-3-mercaptopropanamide, mp 152-157° C. MS (ESI) m/z 595 (M+H)+. Anal. Calcd for $C_{27}H_{42}N_6O_5S_2$: C, 54.52; H, 7.12; N, 14.13; S, 10.78. Found: C, 54.41; H, 7.13; N, 13.85; S, 10.63.

IRM Compound 11 (IRM11)

N-[(4-Amino-1-benzyl-1H-imidazo[4,5-c]quinolin-2-yl)methyl]-3-mercaptopropanamide

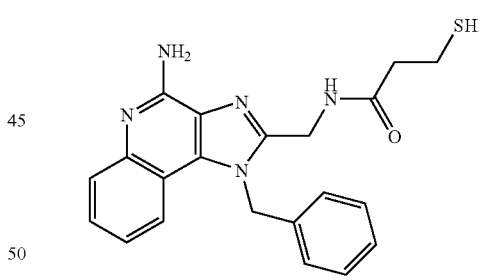

A mixture of 2-(aminomethyl)-1-benzyl-1H-imidazo[4,5-c]quinolin-4-amine (1.0 g, 3.3 mmol) and succinimido 3-(triphenylmethylthio)propanoate (2.2 g, 4.9 mmol) in dichloromethane (33 mL) was stirred overnight at room temperature. The reaction mixture was warmed and the solvent was removed under reduced pressure. Dichloromethane (30 mL) and trifluoroacetic acid (3 mL) were added and the mixture was stirred over the weekend. Additional trifluoroacetic acid was added. After 4 hours, the mixture was concentrated under reduced pressure and purified by flash chromatography on silica gel (gradient elution with a solution of 2% ammonium hydroxide in methanol and chloroform) followed by crystallization from ethyl acetate/acetonitrile. HRMS (ESI) calcd for $C_{21}H_{21}N_5OS+H$ 392.1545, found 392.1534.

IRM Compound 12 (IRM12)

N-(2-{[4-Amino-2-(ethoxymethyl)-1H-imidazo[4,5-c]quinolin-1-yl]oxy}ethyl)-3-mercaptopropanamide

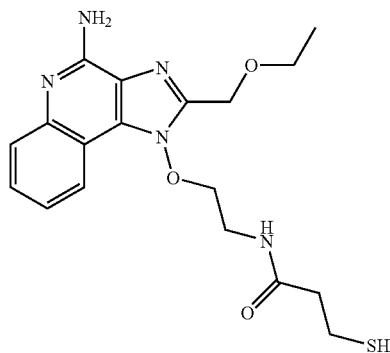 [SMILES: CCOCc1nc2c(N)nc3ccccc3c2n1OCCNC(=O)CCS]

Part A

A mixture of N-(4-chloroquinolin-3-yl)-2-ethoxyacetamide (4.5 g, 18 mmol) and O-benzylhydroxylamine hydrochloride (4.3 g, 27 mmol) in propan-2-ol (100 mL) was heated at 60° C. for 2 days. The mixture was concentrated under reduced pressure and the residue was partitioned between dichloromethane (150 mL) and saturated aqueous sodium bicarbonate (35 mL). The organic layer was dried over potassium carbonate, filtered, and evaporated to yield 5.7 g of crude 1-(benzyloxy)-2-(ethoxymethyl)-1H-imidazo[4,5-c]quinoline that was used directly in Part B.

Part B

A mixture of the material from Part A (5.7 g) and 10% palladium on carbon (0.6 g) in ethanol was hydrogenated on a Parr hydrogenation apparatus at 40 psi ($2.8\times10^5$ Pa) overnight. The mixture was filtered through a pad of CELITE filter agent that was washed afterwards with methanol. The filtrate was concentrated under reduced pressure to afford a solid that was slurried in diethyl ether and isolated by filtration. The solid was washed with diethyl ether to afford 2.9 g of 2-(ethoxymethyl)-1H-imidazo[4,5-e]quinolin-1-ol as a yellow solid.

Part C

To a stirred slurry of 2-(ethoxymethyl)-1H-imidazo[4,5-c]quinolin-1-ol (3.80 g, 15.6 mmol), N-(2-hydroxyethyl)carbamic acid tert-butyl ester (3.9 g, 24 mmol), and triphenylphosphine (6.3 g, 24 mmol) in tetrahydrofuran (120 mL) at 0° C. was added diisopropylazodicarboxylate (4.7 mL, 24 mmol). After 1 hour, the solution was allowed to warm to room temperature. More N-(2-hydroxyethyl)carbamic acid tert-butyl ester (3.9 g, 24 mmol) and triphenylphosphine (6.3 g, 24 mmol) were added, then a solution of diisopropylazodicarboxylate (4.7 mL, 24 mmol) in tetrahydrofuran (10 mL). The reaction mixture was stirred over the weekend, then concentrated under reduced pressure. Dichloromethane (150 mL) was added and the solution was washed with water (2×25 mL). The organic layer was dried over potassium carbonate, filtered, and concentrated under reduced pressure. The solid was washed with diethyl ether/hexanes twice and dried to afford 1.5 g of crude tert-butyl 2-{[2-(ethoxymethyl)-1H-imidazo[4,5-c]quinolin-1-yl]oxy}ethylcarbamate, which was used without purification in Part D below.

Part D

To a stirred solution of tert-butyl 2-{[2-(ethoxymethyl)-1H-imidazo[4,5-c]quinolin-1-yl]oxy}ethylcarbamate (6.0 g) from several batches of Part C in dichloromethane (100 mL) was added m-chloroperbenzoic acid (7.0 g). After about 2 hours, concentrated ammonium hydroxide (35 mL) and water (10 mL) were added. The mixture was cooled in an ice bath and a solution of benzenesulfonyl chloride (3.5 mL) in dichloromethane (25 mL) was added dropwise. The mixture was stirred for 2 hours at room temperature; then dichloromethane (75 mL) and saturated aqueous sodium bicarbonate (35 mL) were added. The aqueous layer was separated and extracted with dichloromethane (2×25 mL). The organic layers were combined, dried over potassium carbonate, filtered, and evaporated to afford an oil. The oil was dissolved in ethanol (50 mL). Concentrated hydrochloric acid (4 mL) was added and the mixture was heated at reflux for 2 days. The reaction mixture was concentrated under reduced pressure. The residue was dissolved in methanol (10 mL) and added to stirred toluene (125 mL) causing an oil to form. The oil was stirred in dichloromethane (75 mL) and 15% sodium hydroxide solution (75 mL) for 2 hours. The layers were separated and the aqueous layer was extracted with dichloromethane (25 mL). The organic layers were combined, dried over potassium carbonate, filtered, and concentrated under reduced pressure to afford 1.3 g of 1-(2-aminoethoxy)-2-(ethoxymethyl)-1H-imidazo[4,5-c]quinolin-4-amine.

Part E

A solution of 1-(2-aminoethoxy)-2-(ethoxymethyl)-1H-imidazo[4,5-c]quinolin-4-amine (30 mg, 0.10 mmol) and succinimido 3-(triphenylmethylthio)propanoate (54 mg, 0.12 mmol) in dichloromethane (1 mL) was stirred for 24 hours at room temperature. Methanol (1 mL) was added and stirring was continued for another 5 days. The mixture was filtered and the filtrate was concentrated. The residue was dissolved in dichloromethane (2 mL) and triethylsilane (0.16 mL) and cooled to 0° C. Trifluoroacetic acid (0.4 mL) was added. The solution was stirred for 30 min; then it was concentrated under reduced pressure. The crude product was purified by flash chromatography on silica gel (gradient elution with a solution of 2% ammonium hydroxide in methanol and chloroform) to provide 18.2 mg of N-(2-{[4-amino-2-(ethoxymethyl)-1H-imidazo[4,5-c]quinolin-1-yl]oxy}ethyl)-3-mercaptopropanamide as a solid. HRMS (ESI) calcd for $C_{18}H_{24}N_5O_3S$+H 390.1600, found 390.1579.

Control Compound 1 (CC1)

N-{2-[2-(Ethoxymethyl)-1H-imidazo[4,5-c]quinolin-1-yl]-1,1-dimethylethyl}-6-[(3-mercaptopropanoyl)amino]hexanamide

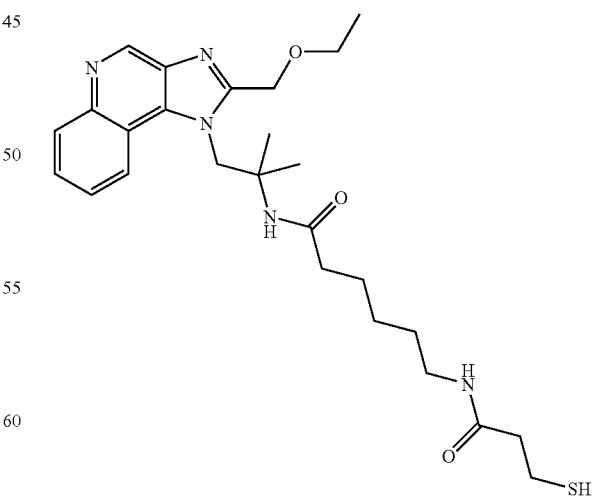

Part A

6-[(tert-Butoxycarbonyl)amino]hexanoic acid (6.81 g, 29.5 mmol), 1-hydroxybenzotriazole (3.98 g, 29.5 mmol), and 1-(3-dimethylaminopropyl)-3-ethylcarbodiimide hydrochloride (EDC) (5.66 g, 29.5 mmol) were added to a 0° C. solution of 2-[2-(ethoxymethyl)-1H-imidazo[4,5-c]quinolin-1-yl]-1,1-dimethylethylamine (which was prepared by acid-mediated deprotection of tert-butyl 2-[2-(ethoxymethyl)-1H-imidazo[4,5-c]quinolin-1-yl]-1,1-dimethylethylcarbamate, which is described in U.S. Patent Publication No. 2004/0091491, 8.00 g, 26.8 mmol) in DMF (80 mL). The solution was stirred at room temperature overnight. More 6-[(tert-butoxycarbonyl)amino]hexanoic acid and EDC were added and the solution was stirred for an additional hour. The solution was partitioned between aqueous sodium bicarbonate and ethyl acetate. The aqueous layer was extracted with ethyl acetate (2×). The organic layers were combined, washed with water and brine, dried over sodium sulfate, filtered, and concentrated under reduced pressure. The crude product was purified by chromatography on silica gel to provide 3.99 g of tert-butyl 6-({2-[2-(ethoxymethyl)-1H-imidazo[4,5-c]quinolin-1-yl]-1,1-dimethylethyl}amino)-6-oxohexylcarbamate as a foam.

Part B

Trifluoroacetic acid (30 mL) was added slowly to a solution of tert-butyl 6-({2-[2-(ethoxymethyl)-1H-imidazo[4,5-c]quinolin-1-yl]-1,1-dimethylethyl}amino)-6-oxohexylcarbamate (3.99 g, 7.82 mmol) in dichloromethane (80 mL) at room temperature. After 1.5 hours, the solution was concentrated under reduced pressure to afford an oil. The oil was dissolved in a small amount of water and concentrated ammonium hydroxide. The resulting basic mixture was extracted with dichloromethane multiple times. The combined organic extracts were dried over sodium sulfate, filtered, and concentrated under reduced pressure to afford 3.4 g of 6-amino-N-{2-[2-(ethoxymethyl)-1H-imidazo[4,5-c]quinolin-1-yl]-1,1-dimethylethyl}hexanamide, which was used in the next step without further purification.

Part C

A solution of 6-amino-N-{2-[2-(ethoxymethyl)-1H-imidazo[4,5-c]quinolin-1-yl]-1,1-dimethylethyl}hexanamide (1.35 g, 3.28 mmol), 3,3'-dithiodipropionic acid (0.345 g, 1.64 mmol), 1-hydroxybenzotriazole (0.443 g, 3.28 mmol), and 1-(3-dimethylaminopropyl)-3-ethylcarbodiimide hydrochloride (0.692, 3.61 mmol) in DMF (10 mL) was stirred at room temperature overnight. The solution was concentrated under reduced pressure and partitioned between saturated aqueous sodium bicarbonate and ethyl acetate/methanol. The organic layers were combined, dried over sodium sulfate, filtered, and concentrated under reduced pressure. The crude product was purified by HPFC on silica gel (gradient elution with CMA/chloroform) to provide the disulfide dimer of N-{2-[2-(ethoxymethyl)-1H-imidazo[4,5-c]quinolin-1-yl]-1,1-dimethylethyl}-6-[(3-mercaptopropanoyl)amino]hexanamide.

Part D

N-{2-[2-(Ethoxymethyl)-1H-imidazo[4,5-c]quinolin-1-yl]-1,1-dimethylethyl}-6-[(3-mercaptopropanoyl)amino]hexanamide (disulfide dimer, 2.14 g, 2.15 mmol) was dissolved in methanol (20 mL). Tris(2-carboxyethyl)phosphine (0.800 g, 2.79 mmol), water (2 mL), and 12.5 M NaOH (0.65 mL, 8.17 mmol) were added. The solution was allowed to stir for 1.5 hours at room temperature, then was cooled in an ice bath. The solution was adjusted to pH 6 with 1 M HCl and the resulting mixture was concentrated under reduced pressure to remove the methanol. The mixture was partitioned between saturated aqueous sodium bicarbonate and dichloromethane. The aqueous layer was extracted multiple times with dichloromethane. The organic phases were combined, washed with water and brine, dried over sodium sulfate, filtered, and concentrated under reduced pressure to provide 1.69 g of N-{2-[2-(ethoxymethyl)-1H-imidazo[4,5-c]quinolin-1-yl]-1,1-dimethylethyl}-6-[(3-mercaptopropanoyl)amino]hexanamide as a white foam that was heated under vacuum to produce a glassy solid.

Colorless glassy solid. MS (ESI) m/z 500 (M+H)$^+$. $^1$H NMR (300 MHz, CDCl$_3$) δ 9.30 (s, 1H), 8.52 (m, 1H), 8.26 (m, 1H), 7.72-7.62 (m, 2H), 5.84 (m, 1H), 5.59 (br s, 1H), 5.18 (br s, 2H), 4.91 (br s, 2H) 3.63 (m, 2H), 3.27 (m, 2H), 2.81 (m, 2H), 2.49 (t, J=6.9 Hz, 2H), 2.05 (t, J=7.5 Hz, 2H), 1.63-1.22 (m, 16H). Anal. calcd for C$_{26}$H$_{37}$N$_5$O$_3$S: C, 62.50; H, 7.46; N, 14.02; S, 6.42. Found: C, 62.23; H, 7.54; N, 13.90; S, 6.65.

Control Compound 2 (CC2)

N-{2-[2-(Ethoxymethyl)-1H-imidazo[4,5-c]quinolin-1-yl]-1,1-dimethylethyl}-6-{[3-(pyridin-2-yldithio)propanoyl]amino}hexanamide

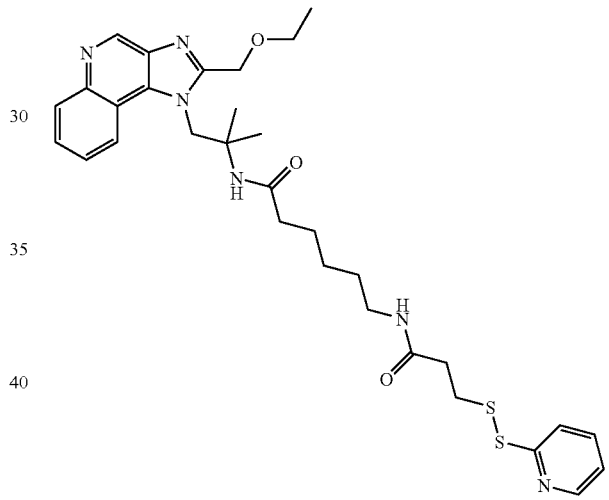

N-{2-[2-(Ethoxymethyl)-1H-imidazo[4,5-c]quinolin-1-yl]-1,1-dimethylethyl}-6-{[3-(pyridin-2-yldithio)propanoyl]amino}hexanamide (0.55 g) was prepared from N-{2-[2-(ethoxymethyl)-1H-imidazo[4,5-c]quinolin-1-yl]-1,1-dimethylethyl}-6-[(3-mercaptopropanoyl)amino]hexanamide (0.83 g) using the procedure described for the preparation of IRM Compound 2. The final product was purified by HPFC on silica gel (gradient elution with 1-10% methanol in dichloromethane) and was isolated as a colorless glassy solid after heating under vacuum.

Colorless glassy solid. MS (ESI) m/z 609 (M+H)$^+$. $^1$H NMR (300 MHz, CDCl$_3$) δ 9.30 (s, 1H), 8.53 (m, 1H), 8.43 (m, 1H), 8.26 (m, 1H), 7.71-7.60 (m, 4H), 7.11 (m, 1H), 6.50 (m, 1H), 5.58 (br s, 1H), 5.19 (br s, 2H), 4.90 (br s, 2H) 3.63 (q, J=6.9 Hz, 2H), 3.28 (m, 2H), 3.07 (m, 2H), 2.60 (m, 2H), 2.07 (t, J=7.5 Hz, 2H), 1.65-1.22 (m, 12H), 1.24 (t, J=6.9 Hz, 3H). Anal. calcd for C$_{31}$H$_{40}$N$_6$O$_3$S$_3$.0.15CH$_3$OH: C, 60.97; H, 6.67; N, 13.70; S, 10.43. Found: C, 60.57; H, 6.75; N, 13.61; S, 10.62.

Control Compound 3 (CC3)

N-{2-[2-(Ethoxymethyl)-1H-imidazo[4,5-c]quinolin-1-yl]-1,1-dimethylethyl}-4-hydrazino-4-oxobutanamide

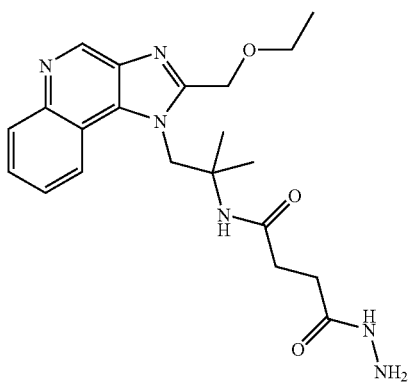 [SMILES: CCOCc1nc2cnc3ccccc3c2n1CC(C)(C)NC(=O)CCC(=O)NN]

Part A

DMF (10 mL) was added to a mixture of 2-[2-(ethoxymethyl)-1H-imidazo[4,5-c]quinolin-1-yl]-1,1-dimethylethylamine (which was prepared by acid-mediated deprotection of tert-butyl 2-[2-(ethoxymethyl)-1H-imidazo[4,5-c]quinolin-1-yl]-1,1-dimethylethylcarbamate, which is described in U.S. Patent Publication No. 2004/0091491, 1.00 g, 3.36 mmol) and succinic anhydride (0.336 g, 3.36 mmol) at room temperature. The mixture was sonicated briefly until a solution formed. The solution was allowed to stand at room temperature for 3 days and then was used in the next step.

Part B

The solution from Part A was cooled to 0° C. and tert-butyl carbazate (0.489 g, 3.70 mmol) and 1-(3-dimethylaminopropyl)-3-ethylcarbodiimide hydrochloride (0.709 g, 3.70 mmol) were added. The mixture was allowed to warm to room temperature and was stirred overnight. More tert-butyl carbazate and 1-(3-dimethylaminopropyl)-3-ethylcarbodiimide hydrochloride were added. After 1 hour, the solution was diluted with water (60 mL) and extracted with ethyl acetate (3×75 mL). The combined organic layers were washed with water, saturated aqueous sodium bicarbonate, and brine. The organic layer was dried over sodium sulfate, filtered, and concentrated under reduced pressure to yield a yellow foam. Chloroform was added to the foam causing a fine white solid to form. The solid was isolated by filtration to provide 0.758 g of tert-butyl 2-[4-({2-[2-(ethoxymethyl)-1H-imidazo[4,5-c]quinolin-1-yl]-1,1-dimethylethyl}amino)-4-oxobutanoyl]hydrazinecarboxylate.

Part C

Trifluoroacetic acid (3 mL) was added slowly to a solution of tert-butyl 2-[4-({2-[2-(ethoxymethyl)-1H-imidazo[4,5-c]quinolin-1-yl]-1,1-dimethylethyl}amino)-4-oxobutanoyl]hydrazinecarboxylate (0.688 g, 1.34 mmol) in dichloromethane (7 mL). The solution was stirred for 2.5 hours, then was concentrated under reduced pressure. The trifluoroacetic acid salt of N-{2-[2-(ethoxymethyl)-1H-imidazo[4,5-c]quinolin-1-yl]-1,1-dimethylethyl}-4-hydrazino-4-oxobutanamide was applied to anion exchange resins, which were eluted with pyridine in methanol to provide N-{2-[2-(ethoxymethyl)-1H-imidazo[4,5-c]quinolin-1-yl]-1,1-dimethylethyl}-4-hydrazino-4-oxobutanamide as a free base, which was purified by HPFC on silica gel (gradient elution, 2-50% CMA in chloroform). The appropriate fractions were concentrated under reduced pressure to yield a foam that was heated under vacuum to afford 0.31 g of N-{2-[2-(ethoxymethyl)-1H-imidazo[4,5-c]quinolin-1-yl]-1,1-dimethylethyl}-4-hydrazino-4-oxobutanamide as a glassy solid.

Glassy solid. MS (ESI) m/z 413 (M+H)$^+$. $^1$H NMR (300 MHz, CDCl$_3$) δ 9.30 (s, 1H), 8.50 (m, 1H), 8.26 (m, 1H), 7.71-7.61 (m, 2H), 7.14 (br s, 1H), 6.13 (br s, 1H), 5.16 (brs, 2H), 4.90 (br s, 2H), 3.88 (br s, 2H), 3.63 (q, J=6.9 Hz, 2H), 2.41 (s, 4H), 1.37 (br s, 6H), 1.24 (t, J=6.9 Hz, 3H). Anal. Calcd for C$_{21}$H$_{28}$N$_6$O$_3$·0.4H$_2$O: C, 60.10; H, 6.92; N, 20.02. Found: C, 60.37; H, 7.01; N, 20.01.

Control Compound 4 (CC4)

N-{2-[2-(Ethoxymethyl)-1H-imidazo[4,5-c]quinolin-1-yl]-1,1-dimethylethyl}-6-{[3-(2,5-dioxo-2,5-dihydro-1H-pyrrol-1-yl)propanoyl]amino}hexanamide

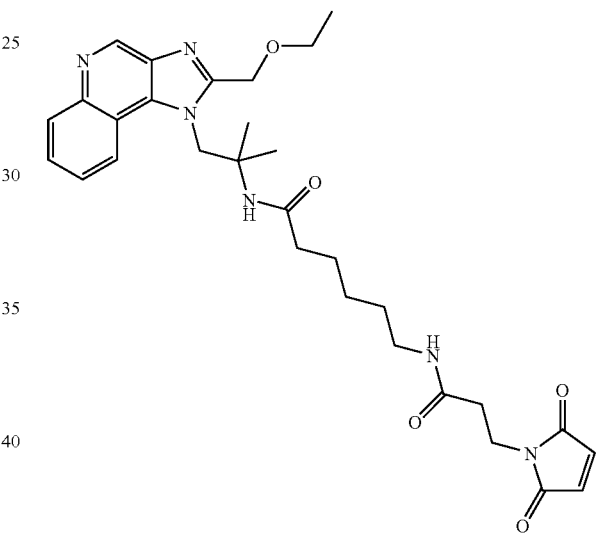

To a solution of 6-amino-N-{2-[2-(ethoxymethyl)-1H-imidazo[4,5-c]quinolin-1-yl]-1,1-dimethylethyl}hexanamide (which was prepared as described above in Parts A and B of Control Compound 1, 163 mg, 0.40 mmol) in dichloromethane (4 mL) at room temperature was added N-succinimidyl-3-maleimidopropionate (111 mg, 0.42 mmol). The mixture was shaken until the reagent dissolved and allowed to stand overnight. The mixture was diluted with dichloromethane (25 mL), washed with 2M aqueous ammonia (10 mL), dried over magnesium sulfate and concentrated under reduced pressure to provide 158 mg of N-{2-[2-(ethoxymethyl)-1H-imidazo[4,5-c]quinolin-1-yl]-1,1-dimethylethyl}-6-{[3-(2,5-dioxo-2,5-dihydro-1H-pyrrol-1-yl)propanoyl]amino}hexanamide.

Light yellow foam, MS (ESI) m/z 563 (M+H)$^+$. $^1$H NMR (300 MHz, CDCl$_3$) δ 9.30 (s, 1H), 8.55 (d, J=7.0 Hz, 1H), 8.31 (m, 1H), 7.69 (m, 2H), 6.68 (s, 2H), 5.79 (m, 1H), 5.57 (br s, 1H), 5.20 (m, 2H), 4.92 (m, 2H), 3.83 (t, J=7.1 Hz, 2H), 3.63 (q, J=6.9 Hz, 2H), 3.22 (q, J=6.7 Hz, 2H), 2.52 (t, J=7.2 Hz, 2H), 2.05 (t, J=7.3 Hz, 2H), 1.55 (m, 12H), 1.25 (t, J=7.0 Hz, 3H).

Preparation of IgG Antibodies

Materials used to prepare the IgG antibody-IRM conjugates can be found in Table 1 below.

TABLE 1

| Material | Source |
| --- | --- |
| Phosphate Buffered Saline (PBS), pH 7.4 | Biosource (Camarillo, CA) |
| Phosphate Buffered Saline (PBS), pH 7.2 | Biosource |
| 1 N Sodium Hydroxide (NaOH) | J.T. Baker (Phillipsburg, NJ) |
| MULTIWELL 12 Well Tissue Culture Plate | Becton Dickenson (Franklin Lakes, NJ) |
| Beckman SYSTMEM GOLD 126 Solvent Module/168 detector chromatography system | Beckman Coulter (Fullerton, CA) |
| SUPERDEX 200 10/300 GL Size Exclusion Column | Amersham Biosciences/GE Healthcare (Piscataway, NJ) |
| 4-succinimidyloxycarbonyl-α-methyl-α-[2-pyridyldithio] toluene (SMPT) | Pierce (Rockford, IL) |
| sulfosuccinimidyl 4-(N-maleimidomethyl)cyclohexane-1-carboxylate (Sulfo-SMCC) | Pierce |
| NHS-PEO$_8$-Maleimide (succinimidyl-[(N-maleimidopropionamido)-octaethyleneglycol] ester) | Pierce |
| Ellman's Reagent (5,5'-dithio-bis-(2-nitrobenzoic acid) | Pierce |
| Traut's Reagent (2-Iminothiolanes•HCl; 2-IT) | Pierce |
| Dimethylsulfoxide (DMSO) | EMD (Gibbstown, NJ) |
| L-cysteine HCl | Pierce |
| 0.5M EDTA, pH 8.0 | Promega (San Luis Obispo, CA) |
| 1M Tris, pH 8.0 | Biosource |
| PD10 Desalting Column | Amersham Biosciences/GE Healthcare |
| Acrodise 13 mm Syringe filter with 0.2 micron HT TUFFRYN membrane | Pall Corporation (East Hills, NY) |
| BCA Protein Assay Kit | Pierce |
| Bovine gamma globulin | Pierce |
| Controlled Protein-Protein Cross-linking Kit | Pierce |
| N-ethylmaleimide (NMI) | Pierce |
| Alexa 488 | Molecular Probe, Carlsbad, CA |

Thiolated IgG Antibody:

The IgG antibody is adjusted to a concentration of 5 to 10 mg/mL in PBS, pH 7.4 containing 5 mM EDTA. Dissolving the 2-IT in PBS, pH 7.4 containing 5 mM EDTA, makes a 5-mg/mL solution of 2-IT. The 2-IT solution is slowly added to the IgG solution while mixing, resulting in the desired molar excess of 2-IT to IgG and incubated for one hour at room temperature. The thiolated IgG is purified by applying the mixture to a desalting column equilibrated with PBS, pH 7.2 containing 5 mM EDTA. 1 mL fractions are collected using an absorbance wavelength of 280 nanometers and the fractions containing thiolated IgG are pooled together. Optionally, the level of activated IgG is determined using a Controlled Protein-Protein Cross-linking Kit.

Heterobifunctional Crosslinking IgG Antibody:

The IgG antibody is adjusted to a concentration of 5 mg/mL in PBS, pH 7.4. The crosslinker (for example, sSMCC, SMPT, or NHS-PEO$_8$-Maleimide) is dissolved in DMSO to a concentration of 5 mg/mL. The crosslinker solution is slowly added to the IgG solution while mixing, resulting in the desired molar excess of the crosslinker to IgG and incubated for one hour at room temperature. The heterobifunctional crosslinking IgG is purified by applying the mixture to a desalting column equilibrated with PBS, pH 7.2 containing 5 mM EDTA. One-milliliter fractions are collected using an absorbance wavelength of 280 nanometers and the fractions containing heterobifunctional crosslinking IgG are pooled together. Optionally, the level of activated IgG is determined using a Controlled Protein-Protein Cross-linking Kit.

Dye Labeled IgG Antibody Control

The IgG antibody is adjusted to a concentration of 3 to 10 milligrams per milliliter in PBS, pH 7.4. The amine reactive dye (for example, Alexa 488) is dissolved in DMSO to a concentration of 5 mg/mL. The amine reactive dye solution is slowly added to the IgG solution while mixing, resulting in the desired molar excess (for example, 8-fold molar excess) of the amine reactive dye to IgG and incubated for one hour at room temperature. The dye labeled IgG is purified by applying the mixture to a desalting column equilibrated with PBS, pH 7.4. One-milliliter fractions are collected measuring the absorbance of the IgG-dye conjugate at 280 nm and the absorbance maximum for the dye ($A_{max}$). Alternately, size exclusion chromatography may be performed using PBS, pH 7.4 as the column running buffer at a flow rate of 1 mL/minute. The fractions containing dye labeled IgG are pooled together. Optionally, the level of activated IgG is determined using a Controlled Protein-Protein Cross-linking Kit.

Preparation of IRM-IgG Antibody Conjugates

Conjugation of Thiolated IgG to Pyridyl Disulfide Modified IRM (pdIRM)

The pdIRM (e.g., IRM2) is dissolved in DMSO at a concentration of 10 mg/mL. The pdIRM is added to the thiolated IgG antibody, as prepared above, at a one to two molar ratio of pdIRM to the 2-IT in the thiolated IgG antibody. The mixture is incubated overnight at room temperature. A 500 mM L-cysteine solution (dissolved in 1 M Tris, pH 8.0) is added to the mixture at 0.01 fold L-cysteine solution to mixture. The IRM-IgG antibody conjugate is purified by size exclusion chromatography using a PBS, pH 7.4 column running buffer, at a flow rate of one mL/min. One-milliliter fractions of mixture are collected and measured at 280 nM. Fractions containing the IgG antibody are pooled and filtered under sterile conditions through a 0.2-micron filter. The concentration of the IRM-IgG antibody conjugate is determined by BCA assay using bovine gamma globulin as a standard. The filtered conjugate is stored at 4° C. for future testing in biological assays.

Conjugation of Heterobifunctional Crosslinking IgG Antibody to Sulfhydryl Modified IRMs (sIRM)

The sIRM (e.g., IRM1) is dissolved in DMSO at a concentration of 10 mg/mL. The sIRM is added to the heterobifunctional crosslinking IgG antibody, as prepared above, at a four-fold molar excess of sIRM to the crosslinker in the heterobifunctional crosslinking IgG antibody. The mixture is incubated overnight at room temperature. A 500 mM L-cysteine solution (dissolved in 1 molar Tris, pH 8.0) is added to the mixture at 0.01 fold L-cysteine solution to mixture. The IRM-IgG antibody conjugate is purified by size exclusion chromatography using a PBS, pH 7.4 column running buffer, at a flow rate of one mL/min. One-milliliter fractions of mixture are collected and measured at 280 nM. Fractions containing the IgG antibody are pooled and filtered under sterile conditions through a 0.2-micron filter. The concentration of the IRM-IgG antibody conjugate is determined by BCA assay using bovine gamma globulin as a standard. The filtered conjugate is stored at 4° C. for future testing in biological assays.

Example 1

IRM1, IRM2, CC1 and CC2 were conjugated to a human anti-CD20 antibody (RITUXAN, Genentech, San Francisco, Calif.). Antibody conjugates to IRM1 and CC1 used the heterobifunctional crosslinking IgG antibody and the antibody-sulfhydryl modified IRMs (sIRM) methods described in the above general method. Specifically, the SMPT crosslinker was mixed with the antibody at a 12-fold molar excess of SMPT to antibody. Antibody conjugates to IRM2 and CC2 used the thiolated IgG antibody and the antibody-pyridyl disulfide modified IRMs (sIRM) methods described in the above general method. Specifically, the 2-IT was mixed with the antibody at a 60-fold molar excess of 2-IT to antibody.

Whole blood from healthy human donors is collected by venipuncture into EDTA containing tubes. Peripheral blood mononuclear cells (PBMC) are separated from whole blood by density gradient centrifugation using Histopaque®-1077 or Ficoll-Paque Plus. The PBMC layer is collected and washed twice with DPBS and resuspended in flow cytometry staining buffer (FACS buffer, Biosource). The PBMCs were added to a 96-well flat bottom sterile tissue culture plate (Costar, Cambridge, Mass. or Becton Dickinson Labware, Lincoln Park, N.J.) to a final PBMC concentration of $1\times10^6$ cells/well. Anti-CD20 or the above prepared conjugates (anti-CD20×IRM) were added to each well at three fold dilutions from 9 µg/mL to 0.004 ug/mL, final concentration in combination with FcR blocking reagent (BD Pharmigen, San Diego, Calif.). The plate was incubated on ice for 15 minutes and then treated with 0.3-µg/mL anti-CD20-Alexa 488 per well. An Isotype (IgG1) negative control (15 µg/mL, Control, BD Pharmigen) and 0.3 µg/mL anti-CD20-Alexa 488 were placed in individual wells. The plate was incubated for 30 minutes on ice in the dark. The plate was centrifuged for 10 minutes at 1350 rpm, and cells were resuspended and washed with FACS buffer twice, resuspended in 200 µL FACS buffer and filtered through a Multi-well filter plate (Pall). Samples were stored overnight at 4° C. and run on a FACSCalibur (Becton Dickenson) the following day. Antibody activities of the conjugates are shown in FIGS. 1 through 4. Activity was measured by the conjugates ability to inhibit the anti-CD20-Alexa 488 stain.

Example 2

Figure 5:
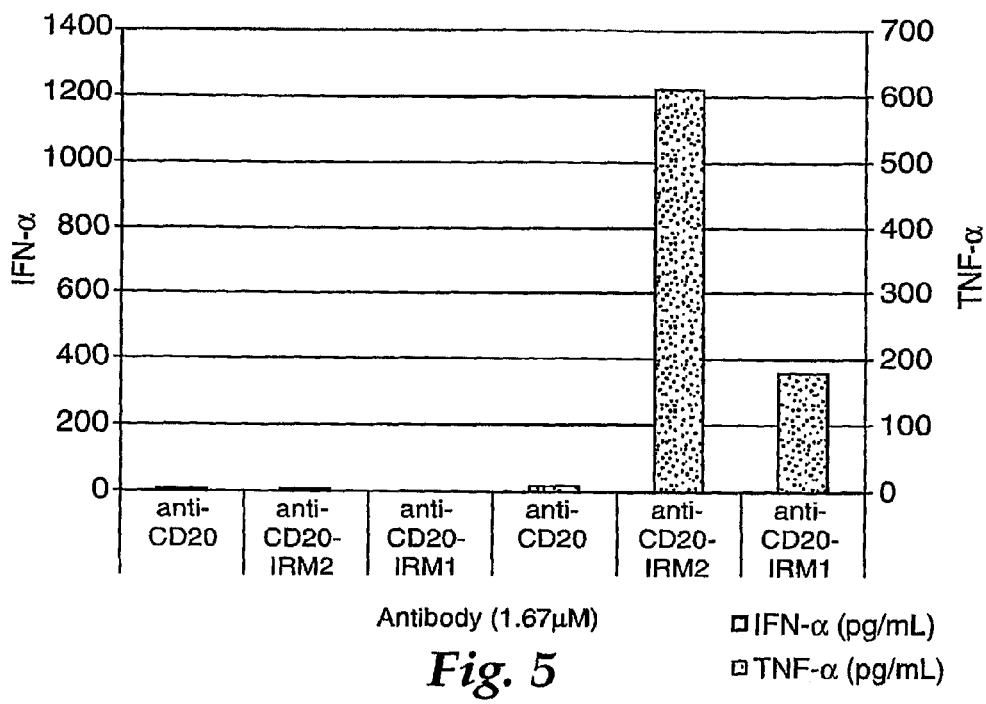
FIG. 5 is a bar graph showing cytokine induction by anti-CD20/IRM conjugates.

Whole blood from healthy human donors is collected by venipuncture into EDTA containing tubes. Peripheral blood mononuclear cells (PBMC) are separated from whole blood by density gradient centrifugation using Histopaque®-1077 or Ficoll-Paque Plus. The PBMC layer is collected and washed twice with DPBS or HBSS and resuspended at $4\times10^6$ cells/mL in RPMI complete media. The PBMCs were added to a 96-well flat bottom sterile tissue culture plate (Costar, Cambridge, Mass. or Becton Dickinson Labware, Lincoln Park, N.J.) to a final PBMC concentration of $2\times10^6$ cells/mL. PBMCs were stimulated overnight at 37° C. in a 5% carbon dioxide atmosphere with 1.67 µM anti-CD20 or the anti-CD20 conjugates prepared in Example 1, based on final antibody concentration. Culture supernatants were analyzed for IFN-α and TNF production using a human IFN-α ELISA (PBL Biomedical Laboratories, Piscataway, N.J.) and human-specific TNF BV™ immunoassay (BioVeris Corp., Gaithersburg, Md.), respectively, with results expressed in pg/mL. Cytokine induction by the conjugates is shown in FIG. 5.

Example 3

IRM2 was conjugated to a mouse anti-CD40 antibody (FGK4.5). The anti-CD40 to IRM2 conjugation method was the same as described in Example 1; however, a 70-fold molar excess of 2-IT to anti-CD40 was used in the preparation of the antibody.

Figure 6:
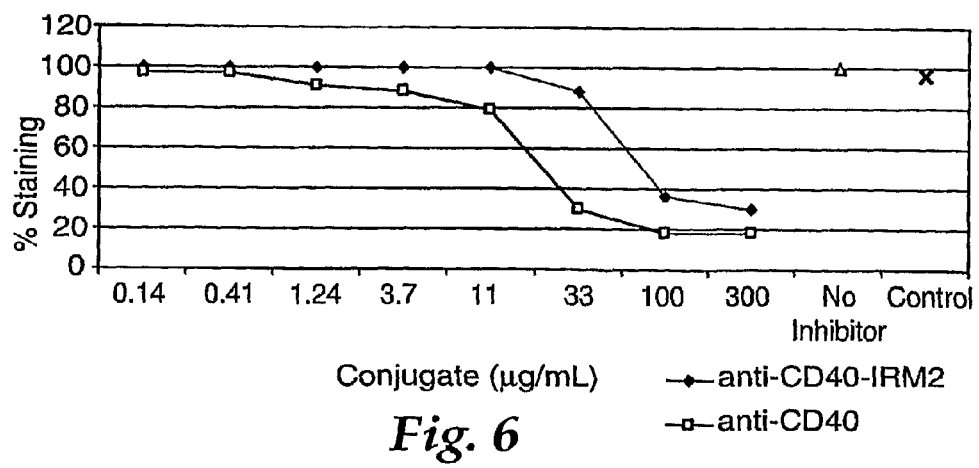
FIG. 6 is a line showing anti-CD40 activity of an IRM/anti-CD40 antibody conjugate.

Mouse spleens were removed from sacrificed C57BL6 mice and splenocytes were isolated from the mice by homogenizing the spleens. Splenocytes were homogenized in Hanks Balance Salt Solution media (Biosource International, Camarillo, Calif.) containing 1% FCS, washed and resuspended in FACS buffer (Biosource International). Splenocytes were plated in a 96-well round bottom sterile tissue culture plate (Costar, Cambridge, Mass. or Becton Dickinson Labware, Lincoln Park, N.J.) to a final cell concentration of $2\times10^6$ cells/well. Anti-CD40 or the above-prepared conjugate were added to each well at three fold dilutions from 300 µg/mL to 0.14 µm, final concentration in combination with mouse FcR blocking reagent (2.4G2). The plate was incubated on ice for 15 minutes and then treated with 25-ug/mL anti-CD40-Alexa 488 per well. An Isotype (IgG2a) negative control (15 µg/mL, Control, BD Pharmigen) and 0.3 µg/ml anti-CD40-Alexa 488 were placed in individual wells. The plate was incubated for 30 minutes on ice in the dark. The plate was centrifuged for 10 minutes at 1500 rpm, and cells were resuspended and washed with FACS buffer twice, resuspended in 100 µL Cytofix buffer (BD Pharmigen) for 15 minutes at room temperature in the dark. Cells were washed and resuspended in 200 µL FACS buffer and filtered through a Multi-well filter plate. Samples were stored overnight at 4° C. and run on a FACSCalibur (Becton Dickenson) the following day. Antibody activities of the conjugates are shown in FIG. 6. Activity was measured by the conjugates ability to inhibit the anti-CD40-Alexa 488 stain.

Example 4

Figure 7:
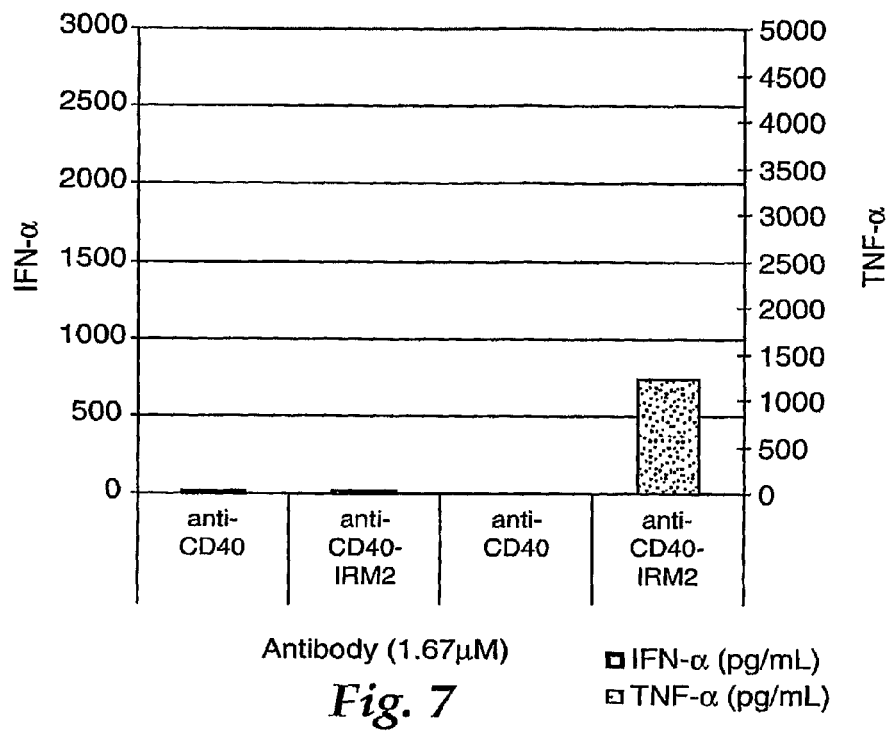
FIG. 7 is a bar graph showing cytokine induction by an IRM/anti-CD40 antibody conjugate.

The anti-CD40 antibody and conjugate, as prepared in Example 3, were tested for cytokine induction as described in Example 2. Cytokine induction by the conjugate is shown in FIG. 7.

Example 5

Figure 8:
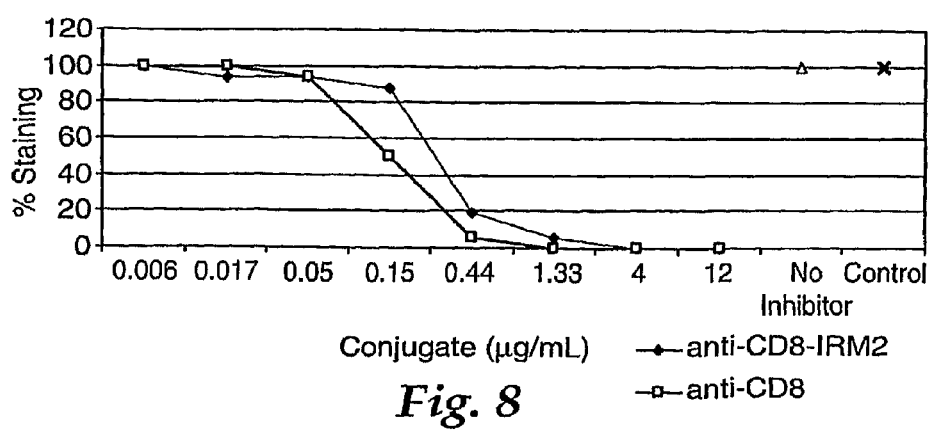
FIG. 8 is a line graph showing anti-CD8 activity of an IRM/anti-CD8 antibody conjugate.
Figure 9:
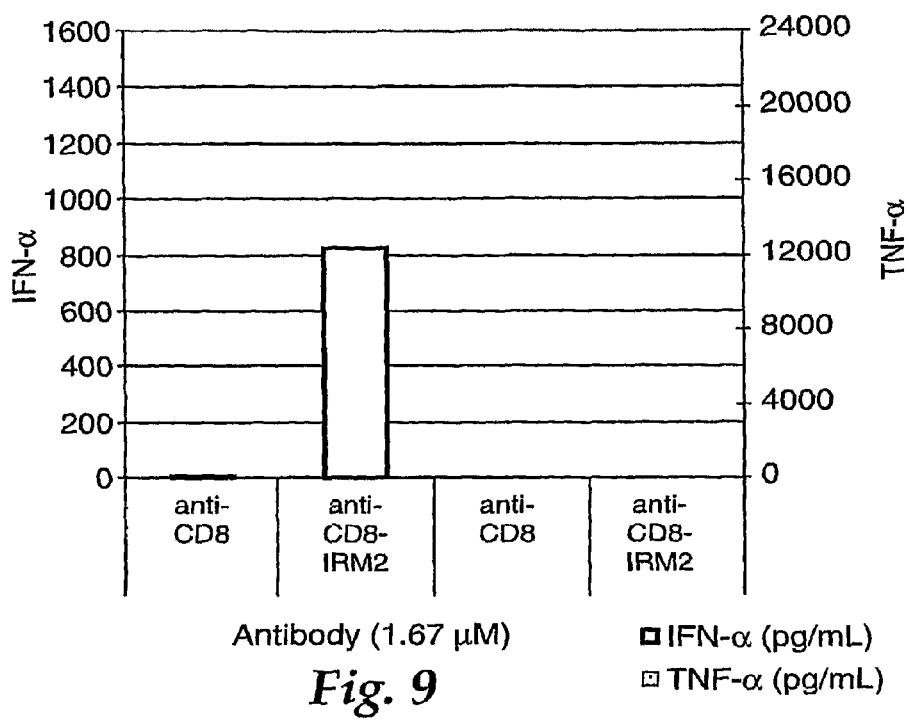
FIG. 9 is a bar graph showing cytokine induction by an IRM-anti-CD8 antibody conjugate.

IRM2 was conjugated to a mouse anti-CD8 antibody (53.6.72; ATCC, Manassas, Va.). The anti-CD8 to IRM2 conjugation method was the same as described in Example 3. The conjugate was tested for antibody activity, as described in Example 3, using three fold dilutions of the conjugate from 12 µg/mL to 0.006 µg/mL and 0.40 µg/mL for the anti-CD8-Alexa 488. The anti-CD8 antibody and conjugate were also tested for cytokine induction as described in Example 2. Antibody activities of the conjugates are shown in FIG. 8. Activity was measured by the conjugates ability to inhibit the anti-CD8-Alexa 488 stain. Cytokine induction by the conjugate is shown in FIG. 9.

Example 6

Part A

A 25 mg/mL ovalbumin (OVA, Sigma) solution was prepared in a reaction buffer. The reaction buffer was a 0.5 M PBS solution containing 0.15 M NaCl and 2 mM EDTA prepared using the manufactures instructions for the Sigma Kit PBS-1. Two OVA control mixtures were prepared by transferring 0.5 mL aliquots of the OVA solution into a 1.5 mL Eppendorf tube and treating with 10 µL of DMSO (Control 1, C1) or 10 µL of a 37 mg/mL solution of N-ethylmaleimide (NMI) in DMSO (Control 2, C2). Additional sample mixtures were prepared by transferring 1.0 mL aliquots of the OVA solution into a 1.5 mL Eppendorf tube and treating with 20 µL of the NMI solution. The mixtures were incubated for 2 to 2.5 hours at room temperature with gentle mixing. The mixtures were each purified over a PD-10 desalting column equilibrated with the reaction buffer, using an absorbance of 280 nM. Fractions were collected, the fractions containing protein were pooled together and the absorbance (280 nM) of the pooled fractions was recorded to determine the final concentration of the modified OVA protein. The concentration of protein in the Control solutions and OVA solutions were 7.5 mg/mL and 12 mg/ml, respectively.

Part B

A 0.1237 M solution of Sulfo-SMCC was prepared in DMSO. The purified OVA solutions from Part A were aliquoted and mixed with 5-fold (5×), 10-fold (10×), 20-fold (20×), or 60-fold (60×) molar excess of Sulfo-SMCC to OVA. The mixtures were incubated for 1.5 to 2 hours at room temperature with gentle mixing. The mixtures were each purified over a PD-10 desalting column and fractions containing protein were pooled and analyzed as described above.

Part C

Solutions of 0.124 M IRM1 and 0.124 M cysteine were made in DMSO. Purified 5×, 10×, 20×, and 60× solutions from Part B were mixed with 12-fold, 17-fold, 27-fold, and 40-fold molar excess of IRM1 to protein, respectively. Purified 10× (10× Cys), 20× (20× Cys), and Control 2 from above were mixed with 17-fold, 27-fold, and 10-fold excess of cysteine to protein, respectively. A 1.5 mL volume of Control 1 was mixed with 40 µL of DMSO. All mixtures were incubated for 45 minutes at room temperature except for the mixtures containing cysteine, which went directly into a 4° C. refrigerator. All samples remained at 4° C. until purification the next day. The mixtures were each purified over a PD-10 desalting column and fractions containing protein were pooled and analyzed as described above. Samples were kept at 4° C. until biological testing was performed.

In Vivo Testing $3 \times 10^6$ chicken ovalbumin-specific OT-I$^+$/GFP$^+$ lymphocytes per mouse were adoptively transferred into syngeneic C57BL/6 mice (Charles River Laboratories, Wilmington, Mass.).

Figure 10:
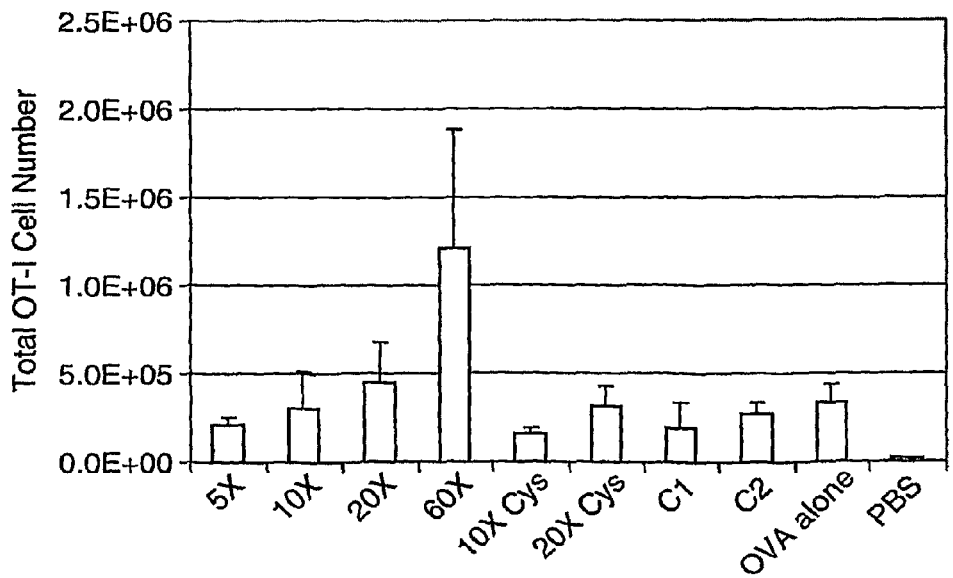
FIG. 10 is a bar graph showing expansion of antigen-specific lymphocytes after immunization with IRM/antigen conjugates.

Twenty-four hours later, the mice were immunized subcutaneously in the rear flank with 100 µL (containing 100 µg of OVA, determined by BCA protein assay, in OVA containing samples) of each of the 5×, 10×, 20×, 60×, 10× Cys, 20× Cys, Control 1 (C1), Control 2 (C2), OVA alone, or PBS alone. Four days after immunization, mice were sacrificed and the inguinal lymph nodes were removed and homogenized into a single cell suspension. The total number of lymphocytes was determined by using a Guava PCA 96 (Guava Technologies, Inc., Hayward, Calif.). Lymphocytes were stained with a propidium iodine (PI)-labeled mouse anti-CD8$^+$ antibody (BD Biosciences Pharmingen, San Diego, Calif.) and the percent OT-I$^+$/GFP$^+$ lymphocytes was determined by flow cytometry gating on PI-CD8$^+$/GFP$^+$ lymphocytes. The total number of OT-I$^+$/GFP$^+$ lymphocytes was determined by multiplying the total number of lymphocytes by the percent OT-I$^+$/GFP$^+$ lymphocytes. Results are shown in FIG. 10.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of making an IRM conjugate comprising:
   covalently attaching a first linker having a first functional group to an IRM compound having immunomodulatory activity, at a site on the IRM compound selected to preserve at least a portion of the immunomodulatory activity of the IRM compound, thereby forming an IRM moiety; and
   allowing the IRM moiety to react with a second moiety having biological activity and a second functional group,
   wherein a covalent bond is formed between the first functional group and the second functional group without use of UV irradiation, thereby forming an IRM conjugate that possesses IRM activity and the biological activity of the second moiety, and wherein the covalent bond formed by the reaction of the first functional group with the second functional group comprises a disulfide linkage, a thioether linkage, a hydrazone linkage, an oxime linkage, a urea linkage, a thiourea linkage, a hydrazine linkage, a hydroxyl amine linkage, or a nitrone linkage.

2. The method of claim 1 wherein the second moiety comprises a second linker having a second functional group attached to a compound having biological activity, at a site on the compound selected to preserve at least a portion of the biological activity of the compound.

3. The method of claim 1 wherein the second moiety is an antigenic moiety.

4. The method of claim 1 wherein the second moiety is a targeting moiety.

5. The method of claim 1 wherein the second moiety comprises a solid support that includes the second functional group.

6. The method of claim 1, wherein the covalent bond formed by the reaction of the first functional group with the second functional group comprises a disulfide linkage or a thioether linkage, and wherein the first functional group comprises a thiol.

7. The method of claim 1, wherein the covalent bond formed by the reaction of the first functional group with the second functional group comprises a hydrazone linkage or a hydrazine linkage, and wherein the first functional group is a 1-4-dioxo-4-hydrazino-butyl.

* * * * *

UNITED STATES PATENT AND TRADEMARK OFFICE
CERTIFICATE OF CORRECTION

PATENT NO.        : 8,951,528 B2
APPLICATION NO.   : 12/280472
DATED             : February 10, 2015
INVENTOR(S)       : Doris Stoermer It is certified that error appears in the above-identified patent and that said Letters Patent is hereby corrected as shown below:

Title Page

<u>Page 2, Column 2 (Other Publications)</u>
Line 20             Delete "Gluteraldehyde" and insert -- Glutaraldehyde --, therefor.

Line 21             Delete "immunogicity" and insert -- immunogenicity --, therefor.

Specification

<u>Column 9</u>
Line 17             Delete "6,239,116," and insert -- 6,239,116: --, therefor.

<u>Column 13</u>
Line 15 (Approx.)   Delete "myelogeous" and insert -- myelogenous --, therefor.

<u>Column 22</u>

Lines 4-9 (Approx.)  Delete " 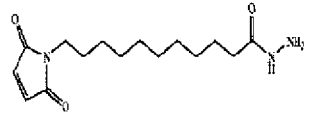 " and insert

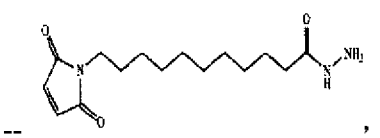 , --, therefor.

Line 22             Delete "trifluoracetic" and insert -- trifluoroacetic --, therefor.

<u>Column 23</u>
Line 53             Delete "J:" and insert -- J. --, therefor.

Signed and Sealed this
Twenty-fourth Day of May, 2016

Michelle K. Lee
*Director of the United States Patent and Trademark Office*

Specification

Column 24
Line 20        Delete "–OC(O)-(4-nitrophenyl);" and insert -- –OC(O)-O-(4-nitrophenyl); --, therefor.

Column 40
Line 41        Delete "-$C_{1-14}$" and insert -- -$C_{1-4}$ --, therefor.

Column 45
Line 9 (Approx.)    Delete "{[3-pyridin-" and insert -- {[3-(pyridine- --, therefor.

Line 59        Delete "chloroform)" and insert -- chloroform). --, therefor.

Column 61
Line 33        Delete "Pharmigen," and insert -- Pharmingen, --, therefor.

Line 37        Delete "Pharmigen," and insert -- Pharmingen, --, therefor.

Column 62
Line 27 (Approx.)    Delete "Pharmigen," and insert -- Pharmingen, --, therefor.

Line 32 (Approx.)    Delete "Pharmigen," and insert -- Pharmingen, --, therefor.